United States Patent
Brooks

(10) Patent No.: US 7,033,771 B2
(45) Date of Patent: Apr. 25, 2006

(54) USE OF INSULIN RESPONSE MODULATORS IN THE TREATMENT OF DIABETES AND INSULIN RESISTANCE

(75) Inventor: Cydney C. Brooks, Arlington, MA (US)

(73) Assignee: Takeda Pharmaceutical Company Limited, (JP)

( * ) Notice: Subject to any disclaimer, the term of this patent is extended or adjusted under 35 U.S.C. 154(b) by 39 days.

(21) Appl. No.: 10/627,311

(22) Filed: Jul. 25, 2003

(65) Prior Publication Data

US 2005/0014194 A1  Jan. 20, 2005

Related U.S. Application Data

(63) Continuation-in-part of application No. PCT/US02/14493, filed on May 8, 2002.

(60) Provisional application No. 60/406,618, filed on Aug. 27, 2002, provisional application No. 60/289,669, filed on May 8, 2001.

(51) Int. Cl.
*G01N 33/53* (2006.01)
*C12Q 1/00* (2006.01)
*C07K 14/00* (2006.01)

(52) U.S. Cl. .......................... 435/7.1; 435/4; 530/350

(58) Field of Classification Search .................. 435/7.1, 435/4; 530/350
See application file for complete search history.

(56) References Cited

U.S. PATENT DOCUMENTS 5,968,764 A * 10/1999 Knowles et al. .............. 435/24

OTHER PUBLICATIONS

Barroso et al., "Transcytosis-associated protein (TAP)/p 115 is a general fusion factor required for binding of vesicles to acceptor membranes", Proc. Natl. Acad. Sci. USA. Jan. 17, 1995; 92(2):527-531.*
Bastiaens et al., "Fluorescence lifetime imaging microscopy: spatial resolution of biochemical processes in the cell", Trends Cell Biol. Feb. 1999; 9(2):48-52.*
Curran et al., "Nonprimate lentiviral vectors" Curr Top Miscrobiol Immunol. 2002; 261:75-105.*
Elazar et al., "ADP-ribosylation factor and coatomer couple fusion to vesicle budding" J Cell Biol. Feb. 1994; 124(4):415-424.*
Fischer A., "Gene therapy: Some results, many problems to solve" Cell Mol Biol. Dec. 2001; 47(8):1269-1275.*
Hemminki A., "From molecular changes to customised therapy" Eur J Cancer. Feb. 2002; 38(3): 333-338.*
Henriksen E.J., "Invtied review: Effects of acute exercise and exercise training on insulin resistance" J Appl Physiol. Aug. 2002; 93(2):788-796.*
Herman et al., "A distinct class of intracellular storage vesicles, identified by expression of the glucose transporter GLUT4" Proc Natl Acad Sci USA. Dec. 20, 1994; 91(26):12750-12754.*
Hertzel et al. "Adenovirus-mediated gene transfer in primary murine adipocytes", J Lipid Res. Jul. 2000; 41(7):1082-1086.*
Lemons et al., "Regulated secretion in platelets: identification of elements of the platelet exocytosis machinery" Blood. Aug. 15, 1997; 90(4): 1490-1500.*
Levine et al., "Binding of the vesicle docking protein p115 to Golgi membranes is inhibited under mitotic conditions" J Biol Chem. Jul. 19, 1996; 271(29):17304-17311.*
Meyer et al., "Gene therapy:progress and challenges" Cell Mol Biol. Dec. 2001; 47(8):1277-1294.*
Nakajima et al., "A cytoskeleton-related gene, USO1, is required for intracellular protein transport in *Saccharomyces cerevisiae*" J Cell Biol. Apr. 1991; 113(2):245-260.*
Nelson et al., "The membrane transport factor Tap/p115 cycles between the Golgi and earlier secretory compartments and contains distinct domains required for its localization and function" J Cell Biol. Oct. 19, 1998 143(2):319-331.*
Richards-Smith et al., "Analyses of proteins involved in vesicular trafficking in platelets of mouse models of Hermansky Pudiak syndrome" Mol Genet Metab. Sep. 1999; 68(1):14-23.*

(Continued)

*Primary Examiner*—Maryam Monshipouri
*Assistant Examiner*—Suzanne M. Mayer
(74) *Attorney, Agent, or Firm*—Lahive & Cockfield, LLP; Debra J. Milasincic

(57) ABSTRACT

Methods of identifying insulin response modulators are provided. Therapeutic methods utilizing compounds identified according to the methods of the invention are also provided. In particular, methods of treating diabetes and insulin resistance are provided.

14 Claims, 4 Drawing Sheets

OTHER PUBLICATIONS

Sapperstein et al., "p115 is a general vesicular transport factor related to the yeast endoplasmic reticulum to Golgi transport factor Uso1p" Proc Natl Acad Sci USA. Jan. 17, 1995; 92(2):522-526.*

Sohda et al., "Phosphorylation of the vesicle docking protein p115 regulates its association with the Golgi membrane" J Biol Chem. Feb. 27, 1998; 273(9):5385-5388.*

Szolloal et al., "Application of fluorescence resonance energy transfer in the clinical laboratory: routine and research" Cytometry. Aug. 15, 1998; 34(4):159-179.*

Sztul et al., "Control of protein traffic between distinct plasma membrane domains. Requirement for a novel 108,000 protein in the fusion of transcytotic vesicles with the apical plasma membrane" J Biol Chem. Jan. 25, 1993; 268(3):1876-1885.*

Sztul et al., "Transcytotic vesicle fustion with plasma membrane" Methods in Enzymology. 1992; 219:49-51.*

Tavare et al., "Lighting up insulin action" Diabet Med. Arp 2001; 18(4):253-260.*

Waters et al., "A novel 115-kD peripheral membrane protein is required for intercisternal transport in the Golgi stack" J Cell Biol. Sep. 1992; 118(5):1015-1026.*

Wattenberg et al., "The molecular control of transport vesicle fusion" New Biol. Jun. 1990; 2(6):505-511.*

Wilson et al., "A fusion protein required for vesicle-mediated transport in both mammalian cells and yeast" Nature. Jun. 1, 1989; 339(6223):355-359.*

Wilson et al., " Intracellular membrane fusion" Trends Biochem Sci. Sep. 1991; 16(9):334-337.*

Han et al., Genbank Accession No. AAC72967 for identification of Mouse TAP (Nov. 12, 1998).*

Misumi Y., Genbank Accession No. BAA25300 for Phosphorylation of the Vesicle (Mar. 17, 1999).*

Genome Sequencing Consortium. Genbank Accession No. NP—062252 for Direct Submission (Dec. 12, 2001).*

Alvarez et al. Genbank Accession No. NP_003706 for the p115-interactive proteins (Jan. 8, 2001).*

Sapperstein et al. Genbank Accession No. P41541 for p115 us a general vesicular transport factor (Apr. 30, 2001).*

Sapperstein et al. Genbank Accession No. P41542 for p115 is a general vesibular transport factor (Apr. 30, 2001).*

Waters et al. Proteins Involved in Vesicular Transport and Membrane Function. Current Opinion in Cell Biology. Aug. 1991. vol. 3, no. 4, pp.615-620.

* cited by examiner

FIG 1A

```
Rat    METPTNDRLQLPRNMIENSMPEEEPDVVDLAKEPCLHPLEPDEVEYEPRGSRLLVRGLGE
Human  MEPFTNDRLQLPRNMIENSMPEEEPDVVDLAKEPCLHPLEPDEVEYEPRGSRLLVRGLGE
       ** *********************************************************

Rat    HEMDEDEEDYESSAKLLGMSFMNRSSGLRNSATGYRQSPDGTCSVPSARTLVICVFVIVV
Human  HRMEEDEEDYESSAKLLGMSFMNRSSGLRNSATGYRQSPDGACSVPSARTMVVCAFVIVV
       * *:***************************************.*******:*:*.****

Rat    AVSVIMVIYLLPRCTFTKEGCHKTNQSAELIQPIATNGKVFPWAQIRLPTAIIPQRYELS
Human  AVSVIMVIYLLPRCTFTKEGCHKKNQSIGLIQPFATNGKLFPWAQIRLPTAVVPLRYELS
       ***********************.*** ****:*****:***********::* *****

Rat    LHPNLTSMTFRGSVTISLQALQDTRDIILHSTGHNISSVTFMSAVSSQEKQVEILEYPYH
Human  LHPNLTSMTFRGSVTISVQALQVTWNIILHSTGHNISRVTFMSAVSSQEKQAEILEYAYH
       *****************:**** * *:********** ************ *****.**

Rat    EQIAVVAPESLLTGHNYTLKIEYSANISNSYYGFYGITYTDKSNEKKNFAATQFEPLAAR
Human  GQIAIVAPEALLAGHNYTLKIEYSANISSSYYGFYGFSYTDESNEKKYFAATQFEPLAAR
       ***:****:**:**************.*******:  ***:*****:************

Rat    SAFPCFDEPAFKATFIIKITRDEHHTALSNMPKKSSVPTEEGLIQDEFSESVKMSTYLVA
Human  SAFPCFDEPAFKATFIIKIIRDEQYTALSNMPKKSSVVLDDGLVQDEFSESVKMSTYLVA
       ******************* ***:.::***********  :.**:***************

Rat    FIVGEMRNLSQDVNGTLVSVYAVPEKIDQVYHALDTTVKLLEFYQNYFEIQYPLKKLDLV
Human  FIVGEMKNLSQDVNGTLVSIYAVPEKIGQVHYALETTVKLLEFFQNYFEIQYPLKKLDLV
       ******:*********** :******:**::***:********:***************

Rat    AIPDFEAGAMENWGLLTFREETLLYDNATSSVADRKLVTKIIAHELAHQWFGNLVTMQWW
Human  AIPDFEAGAMENWGLLTFREETLLYDSNTSSMADRKLVTKIIAHELAHQWFGNLVTMKWW
       **************************. ***:************************:**

Rat    NDLWLNEGFATFMEYFSVEKIFKELNSYEDFLDARFKTMRKDSLNSSHPISSSVQSSEQI
Human  NDLWLNEGFATFMEYFSLEKIFKELSSYEDFLDARFKTMKKDSLNSSHPISSSVQSSEQI
       *****************:*******.************:*********************

Rat    EEMFDSLSYFKGASLLLMLKSYLSEDVFQHAIILYLHNHSYAAIQSDDLWDSFNEVTGKT
Human  EEMFDSLSYFKGSSLLLMLKTYLSEDVFQHAVVLYLHNHSYASIQSDDLWDSFNEVTNQT
       ************.:******.*********::********* **************.:*

Rat    LDVKKMMKTWTLQKGFPLVTVQRKGTELLLQQERFFPSMQPEIQDSDTSHLWHIPISYVT
Human  LDVKRMMKTWTLQKGFPLVTVQKKGKELFIQQERFFLNMKPEIQPSDTSYLWHIPLSYVT
       ****:*****************:**.***:****** .*:****.****:****** ****

Rat    DGRNYSEYRSVSLLDKKSDVINLTEQVQWVKVNTNMTGYYIVHYAHDGWAALINQLKRNP
Human  EGRNYSKYQSVSLLDKKSGVINLTEEVLWVKVNINMNGYYIVHYADDDWEALIHQLKINP
       :*****:*:*********.******:*:*****.**:********.*.**:***:**:**

Rat    YVLSDKDRANLINNIFELAGLGKVPLQMAFDLIDYLRNETHTAPITEALFQTDLIYNLLE
Human  YVLSDKDRANLINNIFELAGLGKVPLKRAFDLINYLGNENHTAPITEALFQTDLIYNLLE
       *************************:: ****:*** ** ********************

Rat    KLGHMDLSSRLVTRVHKLLQNQIQQQTWTDEGTPSMRELRSALLEFACAHSLENCTTMAT
Human  KLGYMDLASRLVTRVFKLLQNQIQQQTWTDEGTPSMRELRSALLEFACTHNLGNCSTTAM
       ***:***:*******:********************************:*.*.**:*  *
```

FIG 1B

```
Rat     KLFDGWMASNGTQSLPTDVMTTVFKVGARTEKGWLFLFSMYSSMGSEAEKDKILEALASS
Human   KLFDDWMASNGTQSLPTDVMTTVFKVGAKTDKGWSFLLGKYISIGSEAEKNKILEALASS
        ****.********************:*:*** **:. * *:******:*********

Rat     ADAHKLYWLMKSSLDGDIIRTQKLSLIIRTVGRQFPGHLLAWDFVKENWNKLVHKFHLGS
Human   EDVRKLYWLMKSSLNGDNFRTQKLSFIIRTVGRHFPGHLLAWDFVKENWNKLVQKFPLGS
        *.:**********:** :******:******:*******************:** ***

Rat     YTIQSIVAGSTHLFSTKTHLSEVQEFFENQSEATLQLRCVQEAFEVIELNIQWMARNLKT
Human   YTIQNIVAGSTYLFSTKTHLSEVQAFFENQSEATFRLRCVQEALEVIQLNIQWMEKNLKS
        ****.******:*********** ********* :******:***:******  :***:

Rat     LTLWL
Human   LTWWL
         
```

USE OF INSULIN RESPONSE MODULATORS IN THE TREATMENT OF DIABETES AND INSULIN RESISTANCE

RELATED APPLICATIONS

This application claims the benefit of U.S. Provisional Application No. 60/406,618, filed Aug. 27, 2002 (pending), entitled "Use of Insulin Response Modulators in the Treatment of Diabetes and Insulin Resistance." This application is also a continuation-in-part of International Patent Application PCT/US02/14493, filed May 8, 2002, entitled "Methods and Reagents for Identifying Insulin Response Modulators and Therapeutic Uses Therefor" (pending), which claims the benefit of U.S. Provisional Application No. 60/289,669, filed May 8, 2001 (expired). The entire contents of the above-referenced applications are incorporated herein by this reference.

BACKGROUND OF THE INVENTION

The regulation of blood glucose levels by insulin is achieved mainly by increased glucose transport exclusively into adipose and skeletal muscle tissue; De Fronzo et al. (1981) *Diabetes* 30:1000–1007 and James et al. (1985) *Am. J. Physiol.* 248:E567–E574. These are the only two tissues that express a specific isoform of the glucose transporter, GLUT4, which mediates the hormonal effect of insulin (for reviews of glucose transporter isoforms and their expression, see Deveskar and Mueckler (1992) *Pediatr. Res.* 31:1–13; Bell et al. (1993) *J. Biol. Chem.* 268:3352–3356; and Baldwin (1993) *Biochim. Biophys. Acta* 1154:17–49). The mechanism of glucose transport activation by insulin is the hormone-dependent enhancement of the rate of GLUT4 translocation from intracellular storage vesicles to the plasma membrane in such a way that the concentration of the transporter on the cell surface increases 10- to 40-fold, depending on the cell type and method of measurement (Zorzono et al. (1989) *J. Biol. Chem.* 264:12358–12363; Holman et al. (1990) *J. Biol. Chem.* 265:18172–18179; Slot et al. (1991) *J. Biol. Chem.* 113:123–135; Slot et al. (1991) *Proc. Nat'l. Acad. Sci. USA* 88:7815–7819; and Smith et al. (1991) *Proc. Nat'l. Acad. Sci. USA* 88:6893–6897). Glucose uptake is increased proportionally to the increment of GLUT4 molecules in the plasma membrane, suggesting that redistribution of transporters is the main, if not only, mechanism that accounts for this effect, Kandror and Pilch (1994) *Proc. Nat'l. Acad. Sca USA* 91:8017–8021.

It is believed that GLUT4 recycles in cells as a constituent of tissue-specific secretory-like microsomal structures, known as "GLUT4-containing vesicles". In addition to GLUT 4, these vesicles have also been determined to include phosphatidylinositol 4-kinase, Del Vecchio and Pilch (1991) *J. Biol. Chem.* 266:13278–13283; vesicle-associated membrane proteins ("VAMPS"), Cain et al. (1992) *J. Biol. Chem.* 267:11681–11684; secretory component-associated membrane proteins ("SCAMPS"), Thoidis et al. (1993) *J. Biol. Chem.* 268:11691–11696; and Laurie et al. (1993) *J. Biol. Chem.* 268:19110–19117; and low molecular weight GTP-binding proteins of the Rab family, Cormont et al. (1993) *J. Biol. Chem.* 268:19491–19497. In addition to the proteins enumerated above, a novel zinc-dependent protease named insulin-responsive aminopeptidase ("IRAP") has been identified and characterized as an important component of GLUT4-containing vesicles (designated previously as gp160, Kandror and Pilch (1994) *Proc. Nat'l. Acad. Sca USA* 91:8017–8021; Kandror et al. (1994) *J. Biol. Chem.* 269:30777–30780; and vp165, Keller et al. (1995) *J. Biol. Chem.* 270:23612–23618. Structurally, IRAP contains a 109-amino acid amino-terminal end which projects into the cytoplasm, a single 22-amino acid transmembrane domain, and a large catalytic domain within the lumen of the vesicle which is responsible for the protein's enzymatic activity, Keller et al. (1995) *J. Biol. Chem.* 270:23612–23618. In the basal state, IRAP is primarily located intracellularly, like GLUT4, but is markedly translocated to the cell surface in response to insulin, Mastick et al. (1994) *J. Biol. Chem.* 269:6089–6092; Kandror and Pilch (1994) *Proc. Nat'l. Acad. Sca USA* 91:8017–8021; Ross et al. (1996) *J. Biol. Chem.* 271:3328–3332; and Ross et al. (1997) *Biochem. Biophys. Res. Commun.* (1997) 239:247–251. Furthermore, it has been suggested that the amino terminus of IRAP, which contains two dileucine motifs and several acidic regions similar to those that occur in GLUT4, functions in the regulation of intracellular trafficking and retention of GLUT4; Waters et al. (1997) *J. Biol. Chem.* 272:23323–23327.

Insulin-responsive glucose transport is essential to the normal functioning and metabolism of fat and muscle tissue in normal animals (e.g., in normal human subjects). Insulin resistance of, for example, skeletal muscle glucose transport is a key defect in the development of impaired glucose tolerance (IGT) and type II diabetes. A more detailed understanding of the molecular mechanisms responsible for insulin-responsive glucose transport would greatly facilitate the development of therapeutic strategies aimed modulating (e.g., increasing) insulin responsiveness and ultimately treating subjects exhibiting IGT and/or having type II diabetes. In particular, the intracellular molecules involved in insulin-responsive glucose transport serve as useful target for modulation in treatment of insulin resistance, IGT and/or type II diabetes.

SUMMARY OF THE INVENTION

The present invention is based, at least in part, on the identification of a heretofore unrecognized biological activity of a protein known in the art as trancytosis-associated protein ("TAP")/p115, referred to interchangeably in the art as p115/TAP, p115, or TAP, and referred to herein as "TAP". In particular, the present invention is based on the discovery that TAP interacts with an important component of GLUT4-containing vesicles, insulin-responsive aminopeptidase ("IRAP"). TAP was identified as an IRAP interacting partner (or IRAP binding protein) by affinity purification of TAP on a matrix comprising amino acid residues 1–109 of IRAP. Binding of TAP to IRAP is competitively inhibited by a bioactive fragment comprising residues 1–109 of IRAP.

TAP has previously been described as a "general fusion factor" required, for example, for cis to medial Golgi transport, for an uncoupled reaction measuring exclusively intra-Golgi fusion, and for fusion of trancytotic vesicles with the apical plasma membrane of polarized epithelial cells. Waters et al. (1992) *J. Cell. Biol.* 118:1015–1026; Elazar et al. (1994) *J. Cell Biol.* 124:415–424; and Sztul et al. (1993) *J. Biol. Chem.* 268:1876–1885. TAP also shares substantial sequence identity with the yeast protein Uso1p, which among other pleiotropic effects has been implicated in endoplasmic reticulum (ER) to Golgi traffic. Nakajima et al. (1991) *J. Cell Biol.* 113:245–260. The role of TAP in intra-Golgi trafficking has been demonstrated to be cell cycle regulated, with binding of TAP to Golgi being inhibited under mitotic conditions. Levine et al. (1996) *J. Biol. Chem.* 271:17304–17311. Moreover, it has been demonstrated that interaction of TAP with Golgi membrane is regulated by the phosphorylation state of TAP. Sohda et al. (1998) *J. Biol. Chem.* 273:5385–5388.

The present inventors are the first to identify a novel role for TAP in GLUT4 vesicle trafficking. In particular, the present inventors have demonstrated that TAP specifically binds IRAP, a critical and insulin-regulatable component of GLUT4 vesicles. Importantly, this TAP:IRAP interaction was identified in differentiated adipocytes, known to be a critical insulin responsive cell type. Based on these data, the present invention features methods of identifying insulin response modulators, in particular, methods that involve TAP and IRAP polypeptide reagents and/or cells that overexpress TAP. The methods (e.g., cell-free and/or cell-based methods) feature determining the ability of a test compound to effect the interaction of TAP, or a bioactive fragment thereof, with IRAP or a bioactive fragment thereof. The methods also feature determining the ability of a test compound to effect the activity of TAP and/or IRAP. In a preferred aspect of the invention, the ability to effect such a TAP:IRAP interaction or TAP and/or IRAP activity is determinative of the compound's ability to modulate insulin responsiveness, e.g., insulin-responsive GLUT4 translocation and, ultimately, glucose uptake.

The present inventors have further demonstrated that TAP is misexpressed in adipocytes from human subjects having various insulin response disorders. In particular, the inventors have demonstrated that TAP expression is lower in insulin resistant subjects and obese diabetic subjects (type II diabetic subjects) as compared to lean subjects. Based on these data, the present invention also features methods (e.g., cell-based methods for identifying modulators (e.g., activators) of TAP expression.

Insulin-response modulators and/or modulators of TAP expression identified according to the methods of the invention are particularly amenable to use in therapeutic modulation of insulin responsiveness and are particularly useful for use in the treatment of insulin-response disorders including, but not limited to insulin resistance, impaired glucose tolerance (IGT) and preferably, type II diabetes. Accordingly, pharmaceutical preparations of insulin-response modulators and/or modulators of TAP expression identified according to the methods of the invention are features as well as methods for treating, for example, insulin resistance, IGT and/or type II diabetes involving administration of said modulators to a subject or patient in need thereof.

Other features and advantages of the invention will be apparent from the following detailed description and claims.

BRIEF DESCRIPTION OF THE DRAWINGS

FIG. 1A-B schematically depicts the amino acid sequence of human and rat IRAP. The N-terminal 109 amino acid fragment used to isolate TAP as an IRAP binding protein is indicated by bold underlining and the corresponding TAP-binding fragment in human IRAP is indicated by underlining. The amino acid sequences of human and rat IRAP are set forth as SEQ ID NO:1 and SEQ ID NO:2, respectively.

FIG. 3 graphically depicts the expression levels of TAP in adipocytes isolated form lean, insulin resistant and obese, diabetic subjects.

DETAILED DESCRIPTION OF THE INVENTION

Figure 2:
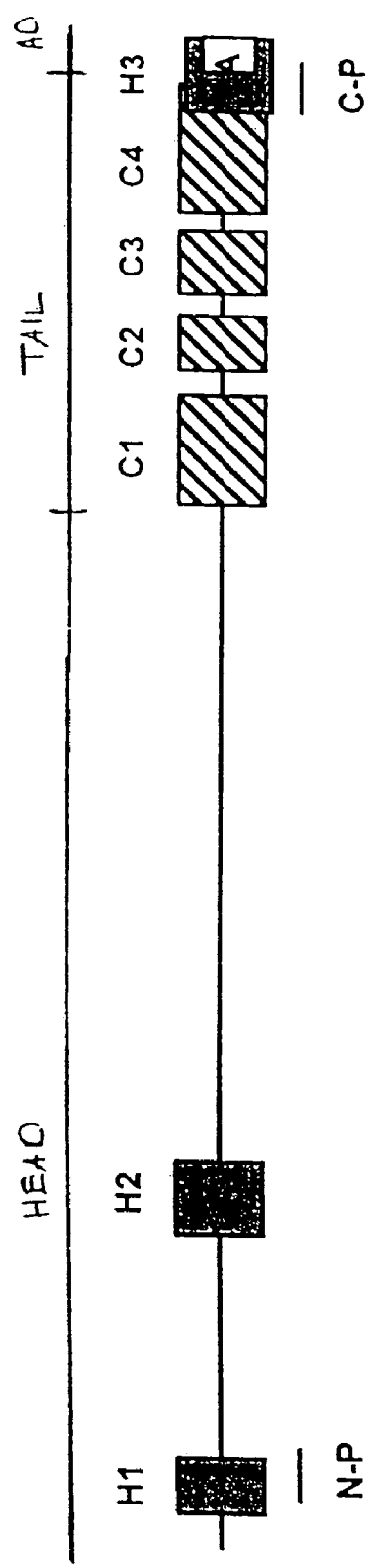
FIG. 2 schematically depicts TAP. Gray boxes indicate regions of homology (H1, H2, H3) with yeast protein Uso1p; lined boxes indicate coiled-coil domains (C1, C2, C3, C4); black box indicates the acidic domain (A). Lines below the protein sequence indicate position of peptides (N-P and C-P) used for generation of TAP antibodies. The amino acid sequence of human TAP is set forth as SEQ ID NO:4.

The present invention is based, at least in part, on the discovery of a previously unrecognized role for TAP (referred to in the art as "trancytosis-associated protein" and p115 interchangeably). In particular, the present invention is based on the discovery of an interaction between TAP and IRAP ("insulin-responsive aminopeptidase"), an important component of insulin-responsive GLUT4-containing vesicles. The TAP/IRAP interaction is believed to be important in the trafficking of GLUT4 vesicles between their intracellular location and the plasma membrane. Modulation of the TAP/IRAP interaction is thus proposed to regulate GLUT4 vesicle trafficking and, consequently, glucose metabolism in two insulin-responsive tissues, namely fat and muscle.

In a first aspect, the present invention features methods of identifying insulin response modulators. In one embodiment, the invention features a method for identifying an insulin response modulator that involves contacting a IRAP-containing composition and a TAP-containing composition with a test compound and determining the ability of the test compound to modulate binding of IRAP to the TAP, such that an insulin response modulator is identified. In another embodiment, the invention features a method for identifying an insulin response modulator that involves contacting a TAP-associated donor vesicle fraction comprising GLUT4 vesicles with a test compound and determining the ability of the test compound to modulate GLUT4 vesicle translocation, such that an insulin response modulator is identified. Determining the ability of the test compound to modulate GLUT4 vesicle translocation can include detecting translocation of a GLUT4 vesicle component to an acceptor vesicle fraction (e.g., detecting changes in GLUT4 levels or IRAP, for example, as compared to an appropriate control). Exemplary donor fractions include GLUT4 vesicle preparations and/or low density microsomal fraction. Exemplary acceptor fractions include plasma membrane fractions. In each of the embodiments described herein, TAP and/or IRAP can be used as full-length proteins. Alternatively, bioactive fragments of TAP and/or IRAP can be used.

In another embodiment, the invention features a method for identifying an insulin response modulator that involves contacting a cell that expresses or overexpressed TAP or a bioactive fragment thereof (optionally in addition to IRAP or a bioactive fragment thereof) with a test compound and determining the ability of the test compound to modulate TAP binding or a TAP-modulated activity (e.g., glucose uptake, GLUT4 vesicle translocation, IRAP translocation and extracellular aminopeptidase activity) such that an insulin response modulator is identified.

TAP (or a TAP bioactive fragment) can be immobilized (e.g., bound to a membrane or to a suitable assay vessel). Assay vesicles can further be detectably labeled (e.g., radioactively labeled) or can include a fluorescent dye for detection. Alternatively, the assay vesicle can be immobilized (e.g., bound to a membrane or to a suitable assay vessel) and optionally can be detectably labeled (e.g., radioactively labeled or fluorescently labeled).

The invention further features a method for identifying an IRAP:TAP modulator, the method involving contacting a composition comprising IRAP and TAP with a test compound and determining the ability of the test compound to enhance or inhibit binding of the IRAP to the TAP, such that the modulator is identified. In yet another embodiment, the invention features a method for identifying an IRAP:TAP modulator, the method involving contacting a composition comprising IRAP or bioactive fragment thereof and TAP or bioactive fragment thereof with a test compound and determining the ability of the test compound to inhibit binding of the IRAP or bioactive fragment thereof to the TAP or bioactive fragment thereof, such that the modulator is identified.

The present invention is also based, at least in part, on the discovery that TAP is misexpressed in preadipocytes isolated from subjects having an insulin response disorder. In particular, it has been found that TAP expression is lower in insulin resistant subjects and obese diabetic subjects (type II diabetic subjects) as compared to lean subjects. Accordingly, in a second aspect, the invention features methods of identifying modulators of TAP expression, in particular, activators of TAP expression or TAP activators.

In a third aspect, modulatory compounds identified by the methods of the present invention (e.g., insulin response modulators or modulators of TAP expression) are also featured (e.g., positive modulators), as are pharmaceutical compositions that include such modulators.

In a fourth aspect, therapeutic methods and/or methods of effecting desired responses in an individual are also featured. In one embodiment, the invention features a method of modulating GLUT4 translocation in a subject that involves administering to the subject an insulin response modulator identified according to one of the screening assays described herein, such that GLUT4 translocation is modulated. In another embodiment, the invention features a method of enhancing glucose clearance in an insulin resistant subject, the method involving administering to the subject an insulin response modulator identified according to one of the screening assays described herein, such that glucose clearing in said subject is enhanced. In yet another embodiment, the invention features a method of regulating (e.g., lowering) blood glucose levels in a subject comprising administering to the subject an insulin response modulator identified according to one of the screening assays described herein, such that blood glucose levels are regulated. In yet another embodiment, the invention features a method of restoring insulin sensitivity in a subject comprising administering to the subject an insulin response modulator identified according to one of the screening assays described herein, such that insulin sensitivity is restored. Preferred subjects are those having an insulin response disorder.

In a related aspect, the invention features therapeutic methods and/or methods of effecting desired responses in an subjects having an insulin response disorder, the methods involving targeting expression of TAP such that a therapeutic effect is achieved in said subjects. In one embodiment, the present invention provides a method for treating type II diabetes by administering to a subject an agent or compound that activates expression of TAP in an amount sufficient to restore normal levels of TAP in said subject. Preferably, the agent or compound is administrated in an amount sufficient to ameliorate at least one symptom of the disease. Related disorders, such as obesity or hyperglycemia can also be treated according to the present invention by administration of agents or compounds that activate or increase expression of TAP.

TAP activators for use in the methods of the present invention can be identified using a variety of appropriate bioassays which test for the ability to stimulate TAP expression or biological activity. The ability of the TAP activators to stimulate TAP expression or activity is preferably specific, i.e., the TAP activator can specifically stimulate TAP mRNA or protein expression or TAP protein activity.

Various aspects of the invention are described in further detail in the following subsections.

So that the invention may be more readily understood, certain terms are first defined.

As used herein, the term "TAP" includes all known forms of TAP and preferably refers to human TAP. The term "TAP protein" refers to any form of TAP polypeptide, for example, full-length TAP polypeptides and TAP fragments (e.g., bioactive fragments, structural and/or functional domains, and the like). The term "TAP nucleic acid molecule" refers to any form of TAP polynucleotide, for example, polynucleotides encoding full-length TAP proteins, polynucleotides encoding TAP fragments (e.g., bioactive fragments, structural and/or functional domains, and the like), and TAP non-coding polynucleotides (e.g., 5' untranslated regions or 3' untranslated regions, regulatory sequences, and the like). The human nucleic acid and amino acid sequences for TAP are set forth as SEQ ID NO:3 and SEQ ID NO:4, respectively.

As used herein, the term "insulin response modulator" refers to an agent or compound that modulates a TAP interaction involving or dependent on IRAP, or a TAP activity involving or dependent on IRAP, or a TAP activity associated with or specific to a vesicle containing IRAP, e.g., a GLUT4-containing vesicle. The ability to modulate a TAP interaction involving or dependent on IRAP, or a TAP activity involving or dependent on IRAP, or a TAP activity associated with or specific to a vesicle containing IRAP, e.g., a GLUT4-containing vesicle, according to the present invention, is predictive of the ability of said agent or compound to modulate insulin responsive vesicle transport, e.g., GLUT4 vesicle transport and, ultimately, insulin responsive uptake.

As used herein, the term "modulator of TAP expression" refers to an agent or compound that modulates TAP nucleic acid and/or TAP protein or polypeptide expression or levels in a cell, e.g., a cell in situ or a cell in vivo.

The term "modulate" means to increase (or activate or upregulate) or decrease (or inhibit or downregulate). For example, modulation of gene expression refers to an activation or upregulation or inhibition or downregulation of expression. Modulation of gene expression includes both direct and indirect modulation of expression. For example, modulation of gene expression includes, but is not limited to, modulation of RNA transcription, modulation of regulatory factors involved in transcription (e.g., activators or co-activators), modulation of regulatory factors involved in RNA degradation, and the like. Modulation of protein expression refers to an activation or upregulation or inhibition or downregulation of protein expression. Modulation of protein activity refers to an activation or upregulation or inhibition or downregulation of protein activity. Modulation of gene expression or protein expression is readily detectable as a change in, for example, mRNA and/or protein levels. Modulation of, for example, protein expression, may also be detectable as a change in processing or cellular localization of a protein. Modulation of protein activity is readily detectable as a change in any assayable molecular or cellular activity characteristic of or specific to the protein of interest. Modulation of activity can also be detected as a change in, for example, the phosphorylation state of a protein whose activity depends on or is regulated by phosphorylation state. As used herein, the term "activation" refers to any upregulation, whether partial or whole, resulting in increased mRNA and/or protein levels.

Preferred "modulators" or "modulatory" compounds include, but are not limited to peptides, peptidomimetics, antibodies or fragment thereof, oligonucleotides, or other small molecules which modulate TAP:IRAP interactions, activities dependant on said interactions, and/or TAP expression. Particularly preferred "modulators" or "modulatory" compounds specifically modulate TAP:IRAP interactions, TAP:IRAP activities and/or TAP expression (e.g., TAP mRNA and/or protein levels) in the cells (e.g., fat and/or muscle cells) of a subject, e.g., a human subject. Additional preferred modulators or modulatory compounds include, but are not limited to, nucleic acid molecules (or fragments of said nucleic acid molecules) including nucleic acid molecules in vectors, as described herein, and protein or polypeptides molecules.

As used herein, the term "diabetes" includes all known forms of diabetes, including type I and type II diabetes, as described in Abel et al., Diabetes Mellitus: A Fundamental and Clinical Text (1996) pp. 530–543.

Modulatory compounds of the invention are typically administered to a subject in "substantially pure" form. The term "substantially pure" as used herein refers to a compound which is substantially free of other molecules or materials with which it is naturally associated. One skilled in the art can purify modulatory compounds using standard purification techniques. For example, when the modulatory compound is a small molecule, the substantially pure preparation will yield a single peak on a chromatography column. When the modulatory compound is a gene therapy vector, the substantially pure polynucleotide will yield a single major band on an agarose gel. The purity of a gene therapy vector can also be determined by restriction mapping. When the modulatory compound is a protein or polypeptide, the substantially pure protein or polypeptide will yield a single major band on a non-reducing polyacrylamide gel. The purity of a protein or polypeptide can also be determined by amino-terminal amino acid sequence analysis.

Cells which are targeted by the methods of the present invention, such as muscle and fat cells, include isolated cells maintained in culture as well as cells within their natural context in vivo (e.g., in fat tissue or muscle tissue, such as pectoralis, triceps, gastrocnemius, quadriceps, and iliocostal muscles).

As used herein, the phrase "insulin response disorder" includes any disease or disorder caused or at least partially caused by a defect in insulin responses or insulin responsiveness. Defects in insulin responses or insulin responsiveness include defects in the synthesis, processing or secretion of insulin, defects in insulin signaling, e.g., defects in insulin receptor expression, regulation, etc. and or defects in the intracellular insulin signaling pathway (in particular, signaling in insulin responsive cells such as fat and muscle cells), defects in insulin degradation and/or recycling, defects in insulin sensitivity, e.g., increased insulin sensitivity or decreased insulin sensitivity (i.e., increased insulin resistance), and the like. Preferred insulin response disorders include but are not limited to type II diabetes and insulin resistance.

The term "small molecule", as used herein, includes any biological or chemical molecule having a molecular weight of less than 500 Dalton.

I. Screening Assays:
  IA. Cell Free Assays

In one embodiment, an assay of the present invention is a cell-free assay in which a TAP polypeptide (or biologically active portion thereof) is contacted with a test compound and the ability of the test compound to bind to the TAP polypeptide (or bioactive fragment thereof) is determined. Binding of the test compound to the TAP polypeptide (or bioactive fragment thereof) can be accomplished, for example, by coupling the test compound or the TAP polypeptide (or bioactive fragment thereof) with a radioisotope or enzymatic label such that binding of the test compound to the TAP polypeptide (or bioactive fragment thereof) can be determined by detecting the labeled compound or polypeptide in a complex. For example, test compounds or polypeptides can be labeled with $^{125}I$, $^{35}S$, $^{14}C$, or $^{3}H$, either directly or indirectly, and the radioisotope detected by direct counting of radioemmission or by scintillation counting. Alternatively, test compounds or polypeptides can be enzymatically labeled with, for example, horseradish peroxidase, alkaline phosphatase, or luciferase, and the enzymatic label detected by determination of conversion of an appropriate substrate to product.

Binding of the test compound to the TAP polypeptide (or bioactive fragment thereof) can also be accomplished using a technology such as real-time Biomolecular Interaction Analysis (BIA). Sjolander, S. and Urbaniczky, C. (1991) Anal. Chem. 63:2338–2345 and Szabo et al. (1995) Curr. Opin. Struct. Biol. 5:699–705. As used herein, "BIA" is a technology for studying biospecific interactions in real time, without labeling any of the interactants (e.g., BIAcore™). Changes in the optical phenomenon of surface plasmon resonance (SPR) can be used as an indication of real-time reactions between biological molecules.

In a preferred embodiment, the assay includes contacting the TAP polypeptide (or biologically active portion thereof) with a TAP target molecule (or a bioactive fragment thereof) to form an assay mixture, contacting the assay mixture with a test compound, and determining the ability of the test compound to interact with the TAP polypeptide (or bioactive fragment thereof), wherein determining the ability of the test compound to interact with the TAP polypeptide (or bioactive fragment thereof) comprises determining the ability of the test compound to preferentially bind to the TAP polypeptide (or the bioactive portion thereof) as compared to the TAP target molecule. In another embodiment, the assay includes contacting the TAP polypeptide (or biologically active portion thereof) with a TAP target molecule (or a bioactive fragment thereof) to form an assay mixture, contacting the assay mixture with a test compound, and determining the ability of the test compound to modulate (e.g., stimulate or inhibit) binding between the TAP polypeptide and the TAP target molecule (or a bioactive fragment thereof). An exemplary TAP target molecule is an IRAP polypeptide (or a bioactive fragment thereof). Another exemplary TAP target molecule is a non-IRAP TAP binding partner. In yet another embodiment, the assay includes contacting a composition comprising a TAP polypeptide (or bioactive fragment thereof), a TAP target molecule (or bioactive fragment thereof) (e.g., a non-IRAP TAP binding partner) and an IRAP polypeptide (or bioactive fragment thereof), with a test compound to form an assay mixture, contacting the assay mixture with a test compound, and determining the ability of the test compound to modulate (e.g., stimulate or inhibit) binding between the TAP polypeptide and the TAP target molecule (or bioactive fragment thereof) and/or IRAP polypeptide (or bioactive fragment thereof).

In another embodiment, the assay is a cell-free assay in which a TAP polypeptide (or bioactive portion thereof) is contacted with a test compound and the ability of the test compound to modulate (e.g., stimulate or inhibit) the activity of the TAP polypeptide (or biologically active portion thereof) is determined.

Determining the ability of the test compound to modulate the activity of a TAP polypeptide (or bioactive fragment thereof) can be accomplished, for example, by determining the ability of the TAP polypeptide to modulate the activity of a TAP binding partner or target molecule (e.g., IRAP) by one of the methods described herein for cell-based assays. For example, the catalytic/enzymatic activity of the target molecule on an appropriate substrate can be determined as previously described (e.g., the aminopeptidase activity of IRAP).

In yet another embodiment, the cell-free assay involves contacting a TAP polypeptide (or biologically active portion thereof) with a TAP target molecule which binds the TAP polypeptide to form an assay mixture, contacting the assay mixture with a test compound, and determining the ability of the test compound to preferentially modulate the activity of a TAP binding partner or target molecule, as compared to the TAP polypeptide (or biologically active portion thereof).

In more than one embodiment of the above assay methods of the present invention, it may be desirable to immobilize either TAP or its binding partner/target molecule to facilitate separation of complexed from uncomplexed forms of one or both of the proteins, as well as to accommodate automation of the assay. Binding of a test compound to a TAP polypeptide, or interaction of a TAP polypeptide with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/TAP fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or TAP polypeptide, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of TAP binding or activity determined using standard techniques.

Additional exemplary TAP fusion proteins include, but are not limited to, chitin binding domain (CBD) fusion proteins, hemagglutinin epitope tagged (HA)-fusion proteins, His fusion proteins (e.g., $His_6$ tagged proteins), FLAG tagged fusion proteins, AU1 tagged proteins, and the like.

Other techniques for immobilizing proteins on matrices can also be used in the screening assays of the invention. For example, either a TAP polypeptide or a TAP target molecule can be immobilized utilizing conjugation of biotin and streptavidin. Biotinylated TAP polypeptide or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with TAP polypeptide or target molecules but which do not interfere with binding of the TAP polypeptide to its target molecule can be derivatized to the wells of the plate, and unbound target or TAP polypeptide trapped in the wells by antibody conjugation. Methods for detecting such complexes, in addition to those described above for the GST-immobilized complexes, include immunodetection of complexes using antibodies reactive with the TAP polypeptide or target molecule (e.g., IRAP), as well as enzyme-linked assays which rely on detecting an enzymatic activity associated with the TAP polypeptide or target molecule.

In yet another aspect of the invention, the TAP polypeptides can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO 94/10300), to identify other proteins, which bind to or interact with TAP ("TAP-binding proteins" or "TAP-target molecules") and are involved in TAP activity. Such TAP-target molecules are also likely to be involved in the regulation of cellular activities modulated by the TAP polypeptides.

At least one exemplary two-hybrid system is based on the modular nature of most transcription factors, which consist of separable DNA-binding and activation domains. Briefly, the assay utilizes two different DNA constructs. In one construct, the gene that codes for a TAP polypeptide is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a TAP-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the TAP polypeptide.

Another exemplary two-hybrid system, referred to in the art as the CytoTrap™ system, is based in the modular nature of molecules of the Ras signal transduction cascade. Briefly, the assay features a fusion protein comprising the "bait" protein and Son-of-Sevenless (SOS) and the cDNAs for unidentified proteins (the "prey") in a vector that encodes myristylated target proteins. Expression of an appropriate bait-prey combination results in translocation of SOS to the cell membrane where it activates Ras. Cytoplasmic reconstitution of the Ras signaling pathway allows identification of proteins that interact with the bait protein of interest, for example, TAP protein. Additional mammalian two hybrid systems are also known in the art and can be utilized to identify TAP interacting proteins. Moreover, at least one of the above-described assays can be utilized to identify IRAP-interacting domains or regions of the TAP protein.

IB. Cell Based Assays

In one embodiment, an assay is a cell-based assay in which a cell which expresses a TAP polypeptide, or biologically active portion thereof, is contacted with a test compound and the ability of the test compound to modulate the activity of the TAP polypeptide, or biologically active portion thereof, determined. The cell, for example, can be of mammalian origin or a yeast cell. The TAP polypeptide, for example, can be expressed heterologously or native to the cell. Determining the ability of the test compound to modulate the activity of a TAP polypeptide, or biologically active portion thereof, can be accomplished by assaying for any of the activities of a TAP polypeptide described herein.

Determining the ability of the test compound to modulate the activity of a TAP polypeptide, or biologically active portion thereof, can also be accomplished by assaying for the activity of a TAP target molecule. In one embodiment, determining the ability of the test compound to modulate the activity of a TAP polypeptide, or biologically active portion thereof, is accomplished by assaying for the ability to bind IRAP or a bioactive portion thereof. In another embodiment, determining the ability of the test compound to modulate the activity of a TAP polypeptide, or biologically active portion thereof, is accomplished by assaying for the activity of IRAP (e.g., by assaying for aminopeptidase activity). In another embodiment, determining the ability of the test compound to modulate the activity of the TAP polypeptide, or biologically active portion thereof, is accomplished by assaying for the activity of a non-IRAP TAP binding partner. In a preferred embodiment, the cell which expresses the TAP polypeptide, or biologically active portion thereof, further expresses a TAP target molecule, or biologically active portion thereof. In another preferred embodiment, the cell expresses IRAP, or biologically active portion thereof. In another preferred embodiment, the cell expresses a non-IRAP TAP binding protein, or biologically active portion thereof. In another preferred embodiment, the cell expresses a IRAP, or biologically active portion thereof, and a non-IRAP TAP binding protein, or biologically active portion thereof. In yet another preferred example, the cell is contacted with a compound (e.g., insulin) which stimulates a TAP-associated activity and the ability of a test compound to modulate the TAP-associated activity is determined.

In another embodiment, an assay is a cell-based assay in which a cell which expresses a TAP polypeptide, or biologically active portion thereof, is contacted with a bioactive peptide derived from a TAP target molecule and a test compound and the ability of the test compound to modulate the activity of the TAP polypeptide, or biologically active portion thereof, determined. In one embodiment, the bioactive peptide is derived from the amino acid sequence of IRAP. In another embodiment, the bioactive peptide corresponds to the N-terminal TAP interacting domain, also referred to herein as the cytoplasmic TAP interacting domain (i.e., amino acids 1–109 of IRAP) or a smaller bioactive fragment thereof (e.g., about amino acids 50–85, preferably about amino acids 55–82 of IRAP). In yet another embodiment, the bioactive peptide corresponds to a trafficking motif of IRAP, i.e., a motif which signals intracellular trafficking from a first to a second cellular location (e.g., membrane location). In yet another embodiment, the bioactive peptide corresponds to domain or motif of a non-IRAP TAP binding protein.

According to the cell-based assays of the present invention, determining the ability of the test compound to modulate the activity of the TAP polypeptide or biologically active portion thereof, can be determined by assaying for any of the native activities of a TAP polypeptide described herein, for example, assaying for GLUT4 translocation, IRAP translocation, IRAP and/or GLUT4 sorting, retention of IRAP and/or GLUT4, intracellular trafficking of IRAP and/or GLUT4-containing vesicles, subcellular fractionation or glucose uptake. IRAP trafficking, for example, can be monitored by labeling cells with biotin (i.e., cell surface biotinylation) followed by detection of labeled IRAP in intracellular fractions, indicating trafficking. Moreover, the activity of the TAP polypeptide or biologically active portion thereof, can be determined by assaying for an indirect activity which is coincident the activity of a TAP polypeptide. For example, the effect of the test compound on the ability of a TAP-expressing cell to uptake glucose in an insulin-dependent manner can be assayed in the presence of the test compound. Furthermore, determining the ability of the test compound to modulate the activity of the TAP polypeptide or biologically active portion thereof, can be determined by assaying for an activity which is not native to the TAP polypeptide, but for which the cell has been recombinantly engineered. For example, the cell can be engineered to express a TAP target molecule which is a recombinant protein comprising a bioactive portion of a TAP target molecule operatively linked to a non-TAP target molecule polypeptide. In an exemplary embodiment, the cytoplasmic domain of the TAP target molecule GLUT4 or IRAP is operatively linked to the transmembrane and extracellular domains of, for example, the transferrin receptor, and the effect of the test compound on the ability of the chimeric protein to traffic intracellularly, determined. (Jonhson et al. (1998) *J. Biol. Chem.* 273:17968–17977 provide an example of the making of such a chimera.) It is also intended that in preferred embodiments, the cell-based assays of the present invention comprise a final step of identifying the compound as a modulator of TAP activity.

II. Assay Reagents

IIA. Test Compounds

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.)).

In a preferred embodiment, the library is a natural product library, e.g., a library produced by a bacterial, fungal, or yeast culture. In another preferred embodiment, the library is a synthetic compound library.

IIB. Antibodies, Bioactive Fragments and Fusion Proteins

Another aspect of the invention features biologically active portions (i.e., bioactive fragments) of TAP or IRAP, including polypeptide fragments suitable for use as immunogens to raise anti-TAP antibodies or IRAP antibodies or to make TAP or IRAP fusion proteins. In one embodiment, TAP or IRAP immunogens or bioactive fragments can be generated from TAP or IRAP isolated from cells or tissue sources by an appropriate purification scheme using standard protein purification techniques. In another embodiment, TAP or IRAP immunogens or bioactive fragments are produced by recombinant DNA techniques. Alternative to recombinant expression, a TAP or IRAP immunogens or bioactive fragments can be synthesized chemically using standard peptide synthesis techniques.

An immunogen, bioactive fragment or fusion protein, as used herein is preferably "isolated" or "purified". The terms "isolated" and "purified" are used interchangeably herein. "Isolated" or "purified" means that the immunogen, bioactive fragment or fusion protein is substantially free of cellular material or other contaminating proteins from the cell or tissue source from which the polypeptide is derived, substantially free of other protein fragments, for example, non-desired fragments in a digestion mixture, or substantially free from chemical precursors or other chemicals when chemically synthesized. The language "substantially free of cellular material" includes preparations in which the polypeptide is separated from other components of the cells from which it is isolated or recombinantly produced. In one embodiment, the language "substantially free of cellular material" includes preparations of polypeptide having less than about 30% (by dry weight) of non-TAP or non-IRAP polypeptide (also referred to herein as a "contaminating protein"), more preferably less than about 20% of non-TAP or non-IRAP polypeptide, still more preferably less than about 10% of non-TAP or non-IRAP polypeptide, and most preferably less than about 5% non-TAP or non-IRAP polypeptide. When the immunogen, bioactive portion or fusion protein is recombinantly produced, it is also preferably substantially free of culture medium, i.e., culture medium represents less than about 20%, more preferably less than about 10%, and most preferably less than about 5% of the volume of the polypeptide preparation. When the immunogen, bioactive fragment or fusion protein is produced by, for example, chemical or enzymatic processing from isolated or purified TAP or IRAP protein, the preparation is preferably free of enzyme reaction components or chemical reaction components and is free of non-desired TAP or IRAP fragments, i.e., the desired polypeptide represents at least 75% (by dry weight) of the preparation, preferably at least 80%, more preferably at least 85%, and even more preferably at least 90%, 95%, 99% or more or the preparation.

The language "substantially free of chemical precursors or other chemicals" includes preparations of polypeptide in which the polypeptide is separated from chemical precursors or other chemicals which are involved in the synthesis of the polypeptide. In one embodiment, the language "substantially free of chemical precursors or other chemicals" includes preparations having less than about 30% (by dry weight) of chemical precursors or reagents, more preferably less than about 20% chemical precursors or reagents, still more preferably less than about 10% chemical precursors or reagents, and most preferably less than about 5% chemical precursors or reagents.

Bioactive fragments of TAP or IRAP include polypeptides comprising amino acid sequences sufficiently identical to or derived from the amino acid sequence of the TAP protein or the IRAP protein, respectively, which include less amino acids than the full length protein, and exhibit at least one biological activity of the full-length protein. Typically, biologically active portions comprise a domain or motif with at least one activity of the full-length protein. A biologically active portion of a TAP or IRAP polypeptide can be a polypeptide which is, for example, 10, 20, 30, 40, 50, 100, 150, 200, 250, 300, 350, 400, 450, 500, 550, 600, 650, 700, 750, 800, 850, 900, 950, 1000 or more amino acids in length. For example, in one embodiment, a bioactive portion of a TAP protein comprises at least an N-terminal head domain. In another embodiment, a bioactive portion of a TAP protein comprises at least a C-terminal tail domain. In yet another embodiment, a bioactive portion of a TAP protein comprises at least a C-terminal acidic domain ("AD"). A preferred activity of a TAP head domain is binding to a second TAP protein or TAP head domain, for example, to inhibit TAP/TAP homodimerization in a cell or vesicle preparation. A preferred TAP tail domain activity is, for example, anchoring to a target membrane. In an exemplary embodiment, the N-terminal globular head region comprises about amino acids 1–650 of human TAP having GenBank Accession No. NP_003706), the C-terminal tail region comprises about amino acids 651–930 of human TAP) and the C-terminal acidic domain ("AD") comprises about amino acids 931–962 of human TAP). In another embodiment, a bioactive portion of an IRAP protein comprises at least a N-terminal or cytoplasmic interacting domain, as defined herein, or a smaller bioactive portion of the N-terminal TAP interacting domain. Moreover, other biologically active portions, in which other regions of the protein are deleted, can be prepared by recombinant techniques and evaluated for one or more of the functional activities of a native TAP or IRAP protein. Mutants of IRAP and/or TAP can also be utilized as assay reagents, for example, mutants having reduced, enhanced or otherwise altered biological properties identified according to one of the activity assays described herein.

To determine the percent identity of two amino acid sequences (or of two nucleotide or amino acid sequences), the sequences are aligned for optimal comparison purposes (e.g., gaps can be introduced in the first sequence or second sequence for optimal alignment). The amino acid residues or nucleotides at corresponding amino acid positions or nucleotide positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i. e., a local alignment). A preferred, non-limiting example of a local alignment algorithm utilized for the comparison of sequences is the algorithm of Karlin and Altschul (1990) *Proc. Natl. Acad. Sci. USA* 87:2264–68, modified as in Karlin and Altschul (1993) *Proc. Natl. Acad. Sci. USA* 90:5873–77. Such an algorithm is incorporated into the BLAST programs (version 2.0) of Altschul, et al. (1990) *J. Mol. Biol.* 215:403–10. BLAST alignments can be generated and percent identity calculated using BLAST protein searches (e.g., the XBLAST program) using TAP, IRAP or a portion thereof as a query, score=50, wordlength=3.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1 997) *Nucleic Acids Research* 25(17):3389–3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, *CABIOS* (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The invention also provides TAP and IRAP chimeric or fusion proteins. As used herein, a TAP or IRAP "chimeric protein" or "fusion protein" comprises a TAP or IRAP polypeptide operatively linked to a non-TAP polypeptide or non-IRAP polypeptide, respectively. A "TAP polypeptide" or "IRAP polypeptide" refers to a polypeptide having an amino acid sequence corresponding to the TAP or IRAP protein, respectively, whereas a "non-TAP polypeptide" or "non-IRAP polypeptide" refers to a polypeptide having an amino acid sequence corresponding to a protein which is not substantially identical to the TAP protein or IRAP protein. Within a fusion protein the TAP or IRAP polypeptide can correspond to all or a portion of a TAP or IRAP protein. In a preferred embodiment, a TAP or IRAP fusion protein comprises at least one biologically active portion of a TAP or IRAP protein, respectively. In another preferred embodiment, a TAP or IRAP fusion protein comprises at least two biologically active portions of a TAP or IRAP protein, respectively. In yet another preferred embodiment, a fusion protein can comprise TAP, or a bioactive portion thereof, operatively linked to IRAP, or a bioactive portion thereof, such that TAP and IRAP, or their respective bioactive portions are brought into close proximity. Within the fusion protein, the term "operatively linked" is intended to indicate that the TAP or IRAP polypeptide and the non-TAP polypeptide or non-IRAP polypeptide are fused in-frame to each other. The non-TAP polypeptide or non-IRAP polypeptide can be fused to the N-terminus or C-terminus of the TAP polypeptide or IRAP polypeptide, respectively.

For example, in one embodiment, the fusion protein is a GST-fusion protein in which the TAP or IRAP sequences are fused to the C-terminus of the GST sequences. In another embodiment, the fusion protein is a chitin binding domain (CBD) fusion protein in which the TAP or IRAP sequences are fused to the N-terminus of chitin binding domain (CBD) sequences. Such fusion proteins can facilitate the purification of recombinant TAP.

Preferably, a chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety. A TAP- or IRAP-encoding nucleic acid can be cloned into such an expression vector such that the fusion moiety is linked in-frame to the TAP or IRAP polypeptide.

A TAP polypeptide or IRAP polypeptide, or a portion or fragment of TAP or IRAP, can also be used as an immunogen to generate antibodies that bind TAP or IRAP or that block TAP/IRAP binding using standard techniques for polyclonal and monoclonal antibody preparation. A full-length polypeptide can be used or, alternatively, the invention provides antigenic peptide fragments for use as immunogens. Preferably, an antigenic fragment comprises at least 8 amino acid residues of the amino acid sequence of TAP (as set forth in GenBank Accession no. NP_003706) or IRAP (as set forth in GenBank Accession no. NP_005566.1) and encompasses an epitope of TAP or IRAP such that an antibody raised against the peptide forms a specific immune complex with TAP or IRAP, respectively. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of TAP or IRAP that are located on the surface of the protein, e.g., hydrophilic regions. Antigenic determinants at the termini of TAP are preferred for the development of antibodies that do not interfere with the TAP:IRAP interaction. Exemplary antigenic determinants include amino acids 40–57 or 888–905 of TAP. Alternatively, interfering antibodies can be generated towards antigenic determinants located within the IRAP interacting domain of TAP. The latter are preferred for therapeutic purposes.

A TAP or IRAP immunogen typically is used to prepare antibodies by immunizing a suitable subject, (e.g., rabbit, goat, mouse or other mammal) with the immunogen. An appropriate immunogenic preparation can contain, for example, recombinantly expressed TAP or IRAP polypeptide or a chemically synthesized TAP or IRAP polypeptide. The preparation can further include an adjuvant, such as Freund's complete or incomplete adjuvant, or similar immunostimulatory agent. Immunization of a suitable subject with an immunogenic TAP or IRAP preparation induces a polyclonal anti-TAP or anti-IRAP antibody response, respectively.

Accordingly, another aspect of the invention pertains to anti-TAP or anti-IRAP antibodies. The term "antibody" as used herein refers to immunoglobulin molecules and immunologically active portions of immunoglobulin molecules, i.e., molecules that contain an antigen binding site which specifically binds (immunoreacts with) an antigen, such as TAP or IRAP. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind TAP. The term "monoclonal antibody" or "monoclonal antibody composition", as used herein, refers to a population of antibody molecules that contain only one species of an antigen binding site capable of immunoreacting with a particular epitope of TAP or IRAP. A monoclonal antibody composition thus typically displays a single binding affinity for a particular TAP or IRAP polypeptide with which it immunoreacts.

Polyclonal anti-TAP or anti-IRAP antibodies can be prepared as described above by immunizing a suitable subject with a TAP or IRAP immunogen, respectively. The antibody titer in the immunized subject can be monitored over time by standard techniques, such as with an enzyme linked immunosorbent assay (ELISA) using immobilized TAP or IRAP. If desired, the antibody molecules can be isolated from the mammal (e.g., from the blood) and further purified by well known techniques, such as protein A chromatography to obtain the IgG fraction. At an appropriate time after immunization, e.g., when the anti-TAP or anti-IRAP antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *PNAS*76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a TAP or IRAP immunogen as described above, and the culture supernatants of the resulting hybridoma cells are screened to identify a hybridoma producing a monoclonal antibody that binds TAP or IRAP, respectively.

Any of the many well known protocols used for fusing lymphocytes and immortalized cell lines can be applied for the purpose of generating an anti-TAP monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind TAP or IRAP, e.g., using a standard ELISA assay.

Alternative to preparing monoclonal antibody-secreting hybridomas, a monoclonal anti-TAP or anti-IRAP antibody can be identified and isolated by screening a recombinant combinatorial immunoglobulin library (e.g., an antibody phage display library) with TAP or IRAP to thereby isolate immunoglobulin library members that bind TAP or IRAP, respectively. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1 993) *EMBO J* 12:725–734; Hawkins et al. (1 992) *J. Mol. Biol.* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc. Acid Res.* 19:4133–4137; Barbas et al. (1991) *PNAS* 88:7978–7982; and McCafferty et al. *Nature* (1990) 348:552–554.

An anti-TAP or anti-IRAP antibody (e.g., monoclonal antibody) can be used to isolate TAP or IRAP, bioactive portions thereof, or fusion proteins by standard techniques, such as affinity chromatography or immunoprecipitation. Anti-IRAP antibodies (or antibodies made according to any of the above-described techniques to any other GLUT4 vesicle component, e.g, GLUT4, or any other preferred donor fraction or acceptor fraction component, can be used to detect protein levels in donor or acceptor fractions as part of certain assay methodologies described herein. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

IIC. Recombinant Expression Vectors and Assay Cells

Another aspect of the invention pertains to vectors, preferably expression vectors, for producing the fusion proteins reagents of the instant invention. As used herein, the term "vector" refers to a nucleic acid molecule capable of transporting another nucleic acid to which it has been linked. A preferred vector is a "plasmid", which refers to a circular double stranded DNA loop into which additional DNA segments can be ligated. In the present specification, "plasmid" and "vector" can be used interchangeably as the plasmid is the most commonly used form of vector.

The recombinant expression vectors of the invention comprise a nucleic acid that encodes, for example TAP or IRAP or a bioactive fragment or TAP or IRAP, in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). The expression vectors can be introduced into host cells to thereby produce proteins, including fusion proteins or peptides. Alternatively, retroviral expression vectors and/or adenoviral expression vectors can be utilized to express the proteins of the present invention.

The recombinant expression vectors of the invention can be designed for expression of TAP or IRAP polypeptides in prokaryotic or eukaryotic cells. For example, TAP or IRAP polypeptides can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990).

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Purified fusion proteins are particularly useful in the cell-free assay methodologies of the present invention.

In yet another embodiment, a TAP or IRAP-encoding nucleic acid is expressed in mammalian cells, for example, for use in the cell-based assays described herein. When used in mammalian cells, the expression vector's control functions are often provided by viral regulatory elements. In another embodiment, the recombinant mammalian expression vector is capable of directing expression of the nucleic acid preferentially in a particular cell type (e.g., tissue-specific regulatory elements are used to express the nucleic acid).

Another aspect of the invention pertains to assay cells into which a recombinant expression vector has been introduced. An assay cell can be prokaryotic or eukaryotic, but preferably is eukaryotic. A preferred assay cell is an adipocyte, for example, a human adipocyte. Adipocytes can be derived from human adipose tissue as undifferentiated cells and expanded ex vivo prior to differentiation for use in the assays of the present invention. Vector DNA can be introduced into prokaryotic or eukaryotic cells via conventional transformation or transfection techniques. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

An assay cell of the invention, can be contacted with a test compound and assayed for any TAP and/or IRAP biological activity in order to identify the compound as an insulin responsive modulator. TAP and/or IRAP biological activities which can be assayed as part of the methodologies of the present invention include, but are not limited to, (1) interaction between TAP or a bioactive fragment thereof with IRAP or a bioactive fragment thereof; (2) modulation of GLUT4 translocation (e.g., exocytosis); (3) modulation of IRAP translocation (e.g., exocytosis); (4) modulation of translocation of another GLUT4 vesicle component; (5) modulation of sorting or retention of IRAP and/or GLUT4; (6) modulation of sorting or retention of another GLUT4 vesicle component; (7) modulation of the entry of IRAP and/or GLUT4 into recycling vesicles; (8) modulation of entry of another GLUT4 vesicle component into recycling vesicles; (9) regulation of intracellular trafficking; and (10) regulation of glucose uptake.

IID. Methods for Identifying Additional TAP Modulators

The invention further provides methods for identifying candidate or test compounds or agents (e.g., proteins or protein fragments, peptides, peptidomimetics, nucleic acid molecules, nucleic acid fragments, antibodies or antibody fragments, small molecules or other drugs) that have an effect on TAP mRNA and/or protein expression.

In one embodiment, an assay is a cell-based assay in which a cell capable of expressing TAP mRNA and/or protein, or a cell which expresses TAP mRNA and/or protein, is contacted with a test compound and the ability of the test compound to modulate, e.g., increase, TAP mRNA and/or protein expression determined. Determining the ability of the compound to modulate, e.g., increase, TAP expression can be accomplished, for example, by detecting the presence or absence or amount of a TAP transcript or protein (e.g., using a probe based on the nucleotide sequences of the present invention or an anti-TAP antibody). Alternatively, the ability of the compound to modulate expression can be determined using a standard transcription-based assay or reporter gene assay. Reporter gene constructs are prepared by operatively linking a reporter gene with at least one transcriptional regulatory element, e.g., a TAP transcriptional regulatory element. Transcriptional control elements include, but are not limited to, promoters, enhancers, and repressor and activator binding sites. Reporter genes include any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979) *Nature* 282: 864–869) luciferase, and other enzyme detection systems, such as beta-galactosidase; firefly luciferase (deWet et al. (1987) *Mol. Cell. Biol.* 7:725–737);

bacterial luciferase (Engebrecht and Silverman (1984) *Proc. Natl. Acad. Sci. USA* 1: 4154–4158; Baldwin et al. (1984) *Biochemistry* 23: 3663–3667); alkaline phosphatase (Toh et al. (1989) *Eur. J. Biochem*. 182: 231–238, Hall et al. (1983) *J. Mol. Appl. Gen*. 2: 101), human placental secreted alkaline phosphatase (Cullen and Malim (1992) *Methods in Enzymol*. 216:362–368) and green fluorescent protein (U.S. Pat. No. 5,491,084; WO 96/23898).

Modulation of TAP expression can be either direct or indirect, for example, via modulation of transcription or translation or by modulation of mRNA and/or protein degradation. In one embodiment, the level of expression of TAP mRNA or protein in the presence of the candidate compound is compared to the level of expression of TAP mRNA or protein in the absence of the candidate compound. The candidate compound can then be identified as a modulator of TAP expression based on this comparison. For example, when expression of TAP mRNA or protein is greater (statistically significantly greater) in the presence of the candidate compound than in its absence, the candidate compound is identified as a stimulator of TAP mRNA or protein expression, i.e., an activator of TAP expression. Alternatively, when expression of TAP mRNA or protein is less (statistically significantly less) in the presence of the candidate compound than in its absence, the candidate compound is identified as an inhibitor of TAP mRNA or protein expression. The level of TAP mRNA or protein expression in the cells can be determined by any art-recognized method for detecting mRNA or protein. For example, mRNA levels can be determined by Northern blot analysis, dot blot analysis, PCR analysis and the like. TAP protein levels can be determined, for example, by Western blot analysis, immunoprecipitation, peptide mapping and/or sequencing, and the like. mRNA expression can also be determined using reporter gene assays, also referred to herein as transcription-based assays. Preferred reporter gene assay systems include, but are not limited to the chloramphenicol acetyltransferase (CAT) and luciferase enzyme assays systems. Preferred cells include, but are not limited to, mammalian and/or yeast cells.

Modulators of TAP expression, in particular, activators of TAP expression, are useful in the therapeutic methods described infra. Additional compounds useful in such methods can be identified by assaying for any of the IRAP-associated TAP activities described supra or, in the alternative, by assaying for any other art recognized TAP activity (see e.g., Waters et al., 1992; Yamakawa et al., 1996; Sonnichsen et al., 1998; Barroso et al., 1995; Nakamura et al., 1997; Levine et al., 1996; and Dirac-Svejstrup et al., 2000; the entire contents of which are incorporated herein by this reference).

III. Methods of Treatment

The present invention further features methods of treatment or therapeutic methods. In one embodiment, the invention features a method of treating a subject (e.g., a human subject in need thereof) with a modulatory compound identified according to the present invention (e.g., an insulin response modulator or a modulator of TAP expression), such that a desired therapeutic effect is achieved.

IIIA. Subjects and Patients

In a preferred aspect, the invention features a method of treating a subject having an insulin response disorder, for example, reduced insulin sensitivity or insulin resistance or diabetes (e.g., Type II diabetes). The present invention also provides for therapeutic methods of treating a subject having pre-diabetes or symptoms thereof, hyperglycemia and/or Type I diabetes. Desired therapeutic effects include a modulation of any TAP-, IRAP- or TAP/IRAP-associated activity, as described herein. A preferred therapeutic effect is modulation of glucose uptake and/or transport. Desired therapeutic effects also include an increase in TAP mRNA expression, TAP protein levels, or TAP activity (e.g., an IRAP-independent TAP activity), as described herein. Desired therapeutic effects also include, but are not limited to curing or healing the subject, alleviating, relieving, altering or ameliorating a disease or disorder in the subject or at least one symptom of said disease or disorder in the subject, or otherwise improving or affecting the health of the subject. A preferred aspect of the invention pertains to methods of modulating TAP/IRAP interactions for therapeutic purposes.

Identification or selection of a subject in need thereof can be accomplished by any skilled medical practitioner or researcher using art-recognized diagnostic skills or techniques. A diabetic subject is a subject, e.g., a human subject, who has been diagnosed as having diabetes (or would be diagnosed as having diabetes) by a skilled medical practitioner or researcher. Preferred tests utilized in diabetes diagnosis include the fasting plasma glucose (FPG)test and the glucose tolerance test, e.g., the 75-g oral glucose tolerance test (OGTT). Exemplary criteria for the diagnosis of diabetes are set forth below.

| Normoglycemia | IFG or IGT ‡ | Diabetes* |
|---|---|---|
| FPG <110 mg/dl | FPG ≧110 and <126 mg/dl (IFG) | FPG ≧126 mg/dl |
| 2-h PG †<140 mg/dl | 2-h PG †≧140 and <200 mg/dl (IGT) | 2-h PG † ≧200 mg/dl |
| | | Symptoms of diabetes and casual plasma glucose concentration ≧200 mg/dl |

‡Midrange values indicating impaired glucose tolerance (IGT), or impaired fasting glucose (IFG).
*A diagnosis of diabetes must be confirmed, on a subsequent day, by measurement of FPG, 2-h PG, or random plasma glucose (if symptoms are present). Fasting is defined as no caloric intake for at least 8 h.
†This test requires the use of a glucose load containing the equivalent of 75 g anhydrous glucose dissolved in water. 2-h PG, 2-h postload glucose.

An insulin resistant subject is a subject, e.g., a human subject, who has been diagnosed as being insulin resistant (or would be diagnosed as being insulin resistant) by a skilled medical practitioner or researcher. An insulin resistant subject can be identified, for example, by determining fasting glucose and/or insulin levels in said subject. In a preferred embodiment, an insulin resistant subject has a fasting glucose level of less than 110 mg/dL and has a fasting insulin level of greater that 30 mU/L.

The effectiveness of treatment of a subject with a modulatory compound of the invention can be monitored by (i) detecting the level of insulin responsiveness or, alternatively, glucose tolerance in the subject prior to treating with the modulator; (ii) detecting the level of insulin responsiveness or, alternatively, glucose tolerance in the subject prior post treatment with the modulator; (iii) comparing the levels pre-administration and post administration; and (iv) altering the administration of the modulator to the subject accordingly. For example, increased administration of the modulator may be desirable if the subject continues to demonstrate insensitive insulin responsiveness.

IIIB. Pharmaceutical Compositions

This invention further pertains to insulin response modulators and/or modulators of TAP expression and/or activity identified by the above-described screening assays. Modulators identified by the above-described screening assays can be tested in an appropriate animal model. For example, a modulator identified as described herein can be used in an animal model to determine the efficacy, toxicity, or side effects of treatment with said modulator. Alternatively, a modulator identified as described herein can be used in an animal model to determine the mechanism of action of such an agent. For example, an agent identified as described herein can be used in an animal model to determine the efficacy, toxicity, or side effects of treatment with such an agent. Alternatively, an agent identified as described herein can be used in an animal model to determine the mechanism of action of such an agent. Preferred animal models include but are not limited to ob/ob, db/db, and mice carrying the lethal yellow mutation. Additional preferred animal models include but are not limited to streptozotocin-induced diabetic rats, obese Zucker rats, and insulin-resistant Otsuka Long-Evans Tokushima Fatty (OLETF) rats. Functional assays for diabetes include, but are not limited to, an insulin sensitivity assay, a glucose tolerance assay, and an ex-vivo glucose uptake by isolated muscle assay also can be performed to monitor the effect of the agent on treated and non-treated animals. Similarly, obesity can be assayed for in these animals, for example, by measuring serum levels of known molecular markers of obesity, such as glucose, insulin, lipids, triglycerides and creatine kinase. Moreover, body weight, and/or fat pad weights can be assayed in these animals. Alternatively, muscle and fat cell differentiation can be observed in these animals. Analysis of such studies should enable a determination of the overall effect of the activator on the disease phenotype in these animal models.

Furthermore, this invention pertains to uses of modulators identified by the above-described screening assays for therapeutic treatments as described infra. Accordingly, the modulators of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g, a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

Pharmaceutical preparations of gene therapy vectors (described infra) can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

IIIC. Gene Therapy

In another aspect of the invention, a gene construct is used as a part of a gene therapy protocol to deliver a nucleic acid encoding a TAP protein, or a biologically active portion thereof. Accordingly, the invention features expression vectors for in vivo or in vitro transfection and expression of TAP (or a biologically active portion thereof) in particular cell types so as to increase the activity of TAP in said cell. Such therapies are particularly useful where the naturally-occurring form of the protein is misexpressed or inappropriately activated.

Expression constructs encoding TAP (or a biologically active portion thereof) may be administered in any biologically effective carrier, e.g. any formulation or composition capable of effectively delivering the recombinant gene to cells in vivo. Approaches include insertion of the DNA encoding TAP (or a biologically active portion thereof) in viral vectors including recombinant retroviruses, adenovirus, adeno-associated virus, and herpes simplex virus-1, or recombinant bacterial or eukaryotic plasmids. Viral vectors infect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $Ca_2PO4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that particular gene constructs provided for in vivo transduction of TAP expression are also useful for in vitro transduction of cells, such as for use in the ex vivo tissue culture systems described below.

A preferred approach for in vivo introduction of nucleic acid into a cell is by use of a viral vector containing nucleic acid, e.g. a cDNA, encoding the TAP protein (or a biologically active portion thereof). Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller (1990) *Blood* 76:271). Thus, recombinant retrovirus can be constructed in which part of the retroviral coding sequence (gag, pol, env) has been replaced by nucleic acid encoding one of the subject proteins rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neuronal cells, in vitro and/or in vivo (see for example Eglitis, et al. (1985) Science 230:1395–1398; Danos and Mulligan (1988) Proc. Natl. Acad. Sci. USA 85:6460–6464; Wilson et al. (1988) Proc. Natl. Acad. Sci. USA 85:3014–3018; Armentano et al. (1990) Proc. Natl. Acad. Sci. USA 87:6141–6145; Huber et al. (1991) Proc. Natl. Acad. Sci. USA 88:8039–8043; Ferry et al. (1991) Proc. Natl. Acad. Sci. USA 88:8377–8381; Chowdhury et al. (1991) Science 254:1802–1805; van Beusechem et al. (1992) Proc. Natl. Acad. Sci. USA 89:7640–7644; Kay et al. (1992) Human Gene Therapy 3:641–647; Dai et al. (1992) Proc. Natl. Acad. Sci. USA 89:10892–10895; Hwu et al. (1993) J. Immunol. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO 94/06920). For instance, strategies for the modification of the infection spectrum of retroviral vectors include: coupling antibodies specific for cell surface antigens to the viral env protein (Roux et al (1989) *PNAS* 86:9079–9083; Julan et al. (1992) *J. Gen Virol* 73:3251–3255; and Goud et al. (1983) *Virology* 163:251–254); or coupling cell surface receptor ligands to the viral env proteins (Neda et al. (1991) *J Biol Chem* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector into an amphotropic vector.

Moreover, use of retroviral gene delivery can be further enhanced by the use of tissue- or cell-specific transcriptional regulatory sequences that control expression of the TAP gene of the retroviral vector.

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *Biotechniques* 6:616; Rosenfeld et al. (1991) Science 252:431–434; and Rosenfeld et al. (1992) Cell 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), adipocytes (Hertzel et al. (2000) *J. Lipid Res*. 41:1082–1086), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) Cell 16:683; Berkner et al., supra; and Graham et al. in Methods in Molecular Biology, E. J. Murray, Ed. (Humana, Clifton, N.J., 1991) vol. 7. pp. 109–127). Expression of the inserted TAP gene can be under control of, for example, the E1A promoter, the major late promoter (MLP) and associated leader sequences, the E3 promoter, or exogenously added promoter sequences.

Yet another viral vector system useful for delivery of the DNA encoding TAP (or a biologically active portion thereof) is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. (1992) *Curr. Topics in Micro. and Immunol*. 158:97–129). It is also one of the few viruses that may integrate its DNA into non-dividing cells, and exhibits a high frequency of stable integration (see for example Flotte et al. (1992) *Am. J. Respir. Cell. Mol. Biol*. 7:349–356; Samulski et al. (1989) *J. Virol*. 63:3822–3828; and McLaughlin et al. (1989) *J. Virol*. 62:1963–1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

In addition to viral transfer methods, such as those illustrated above, non-viral methods can also be employed to cause expression of a TAP (or a biologically active portion thereof) in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject TAP-encoding DNA by the targeted cell. Exemplary gene delivery systems of this type include liposomal derived systems, poly-lysine conjugates, and artificial viral envelopes.

In clinical settings, the gene delivery systems for therapeutic TAP administration can be introduced into a patient by any of a number of methods, each of which is familiar in the art. For instance, a pharmaceutical preparation of the gene delivery system can be introduced systemically, e.g. by intravenous injection. In this case, specific transduction of the protein in the target cells arises from specificity of transfection provided by the gene delivery vehicle, (i.e., cell-type or tissue-type specificity due to transcriptional regulatory sequences controlling recombinant gene expression). In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054–3057). The DNA encoding TAP (or a biologically active portion thereof), can be delivered in a gene therapy construct by electroporation using techniques described, for example, by Dev et al. ((1994) *Cancer Treat Rev* 20:105–115).

The present invention also includes therapeutic methods comprising injecting an area of a subject's body with an effective amount of a naked plasmid DNA compound (such as is taught, for example in Wolff et al., (1990) *Science* 247:1465–1468). A naked plasmid DNA compound comprises a nucleic acid molecule encoding a TAP protein or biologically active portion thereof, operatively linked to a naked plasmid DNA vector capable of being taken up by and expressed in a recipient cell located in the body area. Preferred naked plasmid DNA vectors of the present invention include those known in the art. When administered to a subject, a naked plasmid DNA compound of the present invention transforms cells within the subject and directs the production of TAP protein, or biologically active portion thereof, in the cell.

A naked plasmid DNA compound of the present invention can be injected directly into fat and/or muscle cells or a subject in an amount such that the plasmid is taken up and expressed by the fat and/or muscle cells. As used herein, an effective amount of a naked plasmid DNA to administer to a subject comprises an amount needed to alleviate at least one symptom of the disease or disorder being treated and, preferably, is an amount sufficient to prevent or cure the disease or disorder. The mode of administration, number of doses and frequency of dose capable of being decided upon, in any given situation, by one of skill in the art without resorting to undue experimentation.

The present invention also includes therapeutic methods comprising administering to a subject a genetically-engineered human cell, for example, a genetically-engineered muscle cell or adipocyte, wherein the cell is engineered to overexpress the TAP gene. The terms "genetically-engineered cell" and "recombinant cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

In one embodiment, a recombinant expression vector is introduced into the cell, the vector containing a nucleic acid molecule which encodes a TAP protein (or a biologically active portion thereof). As used herein, the term "vector" refers to a nucleic acid molecule capable of transporting another nucleic acid to which it has been linked. A preferred vector is an "expression vector" which is capable of directing the expression of gene contained therein. In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. In a preferred embodiment, genetic engineering is of a subject or patient's own cells which are isolated from the subject or patient's body, transfected or infected according to the techniques described in detail herein, and reintroduced or returned to the body of the subject or patient.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like.

When using in mammalian cells, e.g., human cells, the expression vector's control functions are often provided by viral regulatory elements. For example, commonly used promoters are derived from polyoma, Adenovirus 2, cytomegalovirus and Simian Virus 40. Alternatively, tissue-specific regulatory elements are used to control expression of the TAP-encoding nucleic acid. Tissue-specific regulatory elements are known in the art. Preferred tissue-specific promoters include fat-specific promoters and muscle-specific promoters.

Vector DNA can be introduced via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual*. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding the TAP protein or can be introduced on a separate vector. Cells stably transfected with the introduced nucleic acid can be identified by drug selection (e.g., cells that have incorporated the selectable marker gene will survive, while the other cells die).

Alternatively, the expression of an endogenous TAP gene can be modified, e.g., increased, within a cell by inserting a heterologous DNA regulatory element into the genome of the cell such that the inserted regulatory element is operatively linked with the endogenous TAP gene. For example, an endogenous TAP gene may be activated by inserting a regulatory element that is capable of promoting the expression of a normally expressed gene product in the cell. The heterologous regulatory element is inserted using techniques, such as targeted homologous recombination, which are well known to those of skill in the art, and described, e.g., in Chappel, U.S. Pat. No. 5,272,071; PCT publication No. WO 91/06667, published May 16, 1991.

Genetically-engineered cells are administered to a subject in need thereof, e.g., a subject having diabetes or an insulin-resistant subject, utilizing any art-recognized method for administering cells to a patient (see e.g., U.S. Pat. No. 5,538,722). In a preferred embodiment, cells are administered via injection, for example, via injection into fat or muscle tissue of the subject in need of treatment.

IIID. Protein Therapy

The present invention also includes therapeutic methods comprising administering to a subject a therapeutically effective dose of TAP protein or a biologically active portion thereof, such that TAP protein levels in said subject are increased or restored to levels detectable in normal or control (e.g., lean) individuals. Preferably, the TAP protein or biologically active portion thereof is made via recombinant means. Biologically active fragments (or portions) of TAP are produced by expression of a fragment (or portion) of a TAP-encoding nucleic acid molecule such that the TAP protein fragment (or portion) is produced recombinantly. Biologically active fragments (or portions) of TAP can be produced by digestion of native or recombinantly produced TAP by, for example, using a protease, e.g., trypsin, thermolysin, chymotrypsin, or pepsin. Computer analysis (using commercially available software, e.g. MacVector, Omega, PCGene, Molecular Simulation, Inc.) can be used to identify proteolytic cleavage sites.

Recombinant proteins (or fragments) can be made according to any well-established methodology for expressing and purifying such proteins. For example, recombinant expression vectors can be designed for expression of TAP protein in prokaryotic or eukaryotic cells. For example, TAP protein can be expressed in bacterial cells such as *E. coli*, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Recombinant expression vectors for expression of TAP protein in eukaryotic cells are described below. More routinely, however, recombinant TAP proteins are produced in prokaryotic cells, for example *E. coli* cells. Examples of suitable *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., Gene Expression Technology: Methods in Enzymology 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res*. 20:2111–2118). Such alteration of nucleic acid sequences of the invention can be carried out by standard DNA modification and synthesis techniques, e.g., mutagenesis techniques.

In another embodiment, the TAP expression vector is a yeast expression vector. Examples of vectors for expression in yeast *S. cerevisiae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, TAP protein can be expressed in insect cells using baculovirus expression vectors. Baculovirus vectors available for expression of proteins in cultured insect cells (e.g., Sf 9 cells) include the pAc series (Smith et al. (1983) *Mol. Cell Biol*. 3:2156–2165) and the pVL series (Lucklow and Summers (1989) *Virology* 170:31–39).

A prokaryotic, yeast or insect cell (into which a recombinant expression vector encoding a TAP protein has been introduced) is then cultured in a suitable medium such that the TAP protein is produced and the TAP protein is then isolated or purified from the medium or the host cell. When the TAP protein or biologically active portion thereof is recombinantly produced, it is also preferably substantially free of culture medium, i.e., culture medium represents less than about 20%, more preferably less than about 10%, and most preferably less than about 5% of the volume of the protein preparation. In some instances it may be desirable to utilize a solubilizing agent such that the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-1 14, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]- 2-hydroxy-1-propane sulfonate (CHAPSO), or N-dodecyl=N,N-dimethyl-3-ammonio-1-propane sulfonate.

The invention also provides for reduction of the TAP proteins to generate mimetics, e.g. peptide or non-peptide agents, which are able to function in a manner similar to naturally-occurring TAP yet have improved therapeutic properties as compared to naturally-occurring TAP. A mimetic can be obtained by, for example, screening libraries of natural and synthetic compounds as disclosed herein that are capable of functioning in a manner similar to naturally-occurring TAP. A mimetic can also be obtained by, for example, rational drug design.

IIIE. TAP Activating Antibodies

The present invention also includes therapeutic methods comprising administering to a subject a therapeutically effective dose of an TAP activating antibody or biologically active portion thereof, such that TAP biological activity in said subject is increased or restored to levels detectable in normal or control (e.g., lean) individuals. Preferred antibodies include monoclonal antibodies, including humanized, chimeric and human monoclonals or fragments thereof. To generate such antibodies, a proteolytic or synthetic TAP fragment (alone or linked to a suitable carrier or hapten) can be used to immunize a subject (e.g., a mammal including, but not limited to a rabbit, goat, mouse or other mammal). For example, the methods described in U.S. Pat. Nos. 5,422,110; 5,837,268; 5,708,155; 5,723,129; and 5,849,531, can be used and are incorporated herein by reference. The immunogenic preparation can further include an adjuvant, such as Freund's complete or incomplete adjuvant, or similar immunostimulatory agent. Immunization of a suitable subject with an immunogenic proteolytic or synthetic TAP fragment preparation induces a polyclonal anti-TAP antibody response. The anti-TAP antibody titer in the immunized subject can be monitored over time by standard techniques, such as with an enzyme linked immunosorbent assay (ELISA) using immobilized TAP. Subsequently, the sera from the immunized subjects can be tested for their TAP stimulatory activity using any of the bioassays described herein.

Alternatively, it is also possible to immunize subjects with plasmids expressing TAP using DNA immunization technology, such as that disclosed in U.S. Pat. No. 5,795,872, Ricigliano et al., "DNA construct for immunization" (1998), and in U.S. Pat. No. 5,643,578, Robinson et al., "Immunization by inoculation of DNA transcription unit" (1997).

The antibody molecules directed against TAP can be isolated from the mammal (e.g., from the blood) and further purified by well known techniques, such as protein A chromatography to obtain the IgG fraction. At an appropriate time after immunization, e.g., when the anti-TAP antibody titers are highest, antibody-producing cells can be obtained from the subject and used to prepare e.g., monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.,* 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a TAP immunogen as described above, and the culture supernatants of the resulting hybridoma cells are screened to identify a hybridoma producing a monoclonal antibody that binds TAP.

Any of the many well known protocols used for fusing lymphocytes and immortalized cell lines can be applied for the purpose of generating an anti-TAP monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind TAP, e.g., using a standard ELISA assay. The antibodies can then be tested for TAP stimulatory activity using, for example, the assays described herein.

In another embodiment, the method involves administering to an isolated tissue or cell line from the subject a modulatory compound identified according to the methodology described herein, such that a desired effect is achieved. In another embodiment, the method involves genetically-engineering a tissue or cell line, e.g., a tissue or cell line from a subject or patient, such that TAP expression or activity is activated. Tissue or cell lines treated ex vivo with a TAP activator or genetically-engineered in accordance with the methodologies of the present invention are preferably introduced into the subject or patient after ex vivo manipulation, such that a desired therapeutic effect is achieved.

IV. Diagnostic Assays

The present invention is based at least in part on the discovery that TAP and IRAP are binding partners and a role for this interaction in regulating normal insulin responsiveness in a subject is described. The invention is further based on the discovery that aberrant expression of TAP is associated with abnormal insulin responsiveness. Accordingly, the present invention also features diagnostic assays, for determining aberrant TAP expression or activity, in the context of a biological sample (e.g., blood, serum, cells, tissue) to thereby determine whether an individual is afflicted with a disease or disorder (e.g., abnormal insulin responsiveness), or is at risk of developing such a disorder. The invention also provides for prognostic (or predictive) assays for determining whether an individual is at risk of developing such a disorder (e.g., a disorder associated with aberrant TAP expression or activity). Such assays can be used for prognostic or predictive purpose to thereby phophylactically treat an individual prior to the onset of a disease or disorder. A preferred agent for detecting TAP protein is an antibody capable of binding to TAP protein, preferably an antibody with a detectable label. The term "biological sample" is intended to include tissues, cells and biological fluids isolated from a subject, as well as tissues, cells and fluids present within a subject. The invention also encompasses kits for the detection of aberrant expression or activity of TAP in a biological sample. For example, the kit can comprise a labeled compound or agent capable of detecting TAP in a biological sample; means for determining the amount of TAP in the sample; and/or means for comparing the amount of TAP in the sample with a standard. The compound or agent can be packaged in a suitable container. The kit can further comprise instructions for using the kit.

This invention is further illustrated by the following examples which should not be construed as limiting. While they are typical of those that might be used, other procedures known to those skilled in the art may alternatively be used. Other uses for the methods of the invention will be apparent to one of ordinary skill in the art from the following Examples and Claims. The contents of all references, patents and published patent applications cited throughout this application are hereby incorporated by reference.

EXAMPLES

The present invention relates to the fields of diabetes and insulin resistance. Agents that would act as insulin-mimetics will permit restoration of insulin sensitivity and result in lower blood glucose levels. Insulin resistance results from the inability of normally insulin-responsive tissues to respond to the hormone. In normally function muscle and fat cells, insulin binds to its receptor on the surface of the cell and initiates a series of intracellular events including the transport of glucose into the cell. This glucose transport is the key event that regulates the level of glucose in the blood and maintains normoglycemia. The inability to take up glucose into these cells is a condition called insulin resistance and in often found in the diabetic or pre-diabetic state. The activity and regulation of the molecule that transports glucose into the cell has been widely studied in the hopes that understanding of its function may lead to the ability to alter that function and restore responsiveness to insulin. The insulin-responsive glucose transporter, GLUT4, is found in intracellular vesicles that are located in an insulin-sensitive intracellular compartment. In the absence of insulin, these GLUT4-containing vesicles (G4Vs) are retained in the cytosol of the cell. Upon insulin binding to its receptor at the surface of the cell the G4Vs move from this compartment to the cell surface where GLUT4 is then at the cell surface and can transport glucose into the cell. The trafficking and regulation of GLUT4, as well as other proteins that are associated with G4Vs are beginning to be understood. One protein that has been shown to be present in G4Vs is the insulin-responsive aminopeptidase (IRAP). In addition to being co-localized with GLUT4, IRAP translocates to the plasma membrane in response to insulin like GLUT4 does. IRAP is a transmembrane protein with a large extracellular aminopeptidase domain and a smaller (109 amino acids) amino terminal domain that is intracellular. It has been hypothesized that there is a protein that interacts with a component of G4Vs and retains the vesicles in the cytosol. Insulin-stimulated events result in the release of this tether and subsequent movement of GLUT4 and IRAP to the cell surface. IRAP has been implicated in the tethering of G4Vs; the microinjection of the cytoplasmic domain of IRAP induces the translocation of G4Vs in the absence of insulin. To identify candidate proteins involved in this tethering of G4Vs, a biochemical screen was set up to identify proteins that interact with IRAP.

Example 1

Identification and Characterization of TAP as an IRAP Binding Protein

To identify potential IRAP-binding proteins (IBPs), a fusion protein was generated, expressed in and purified from *E. coli* and used as an affinity reagent to bind proteins that interact with IRAP. The cDNA coding for the cytoplasmic domain of IRAP, corresponding to amino acids 1–109, was subcloned into the pTYB4 vector from the IMPACT T7 System (New England Biolabs). This system permits folding of the amino terminus of IRAP in a manner similar to the native conformation and is therefore accessible to potential binding proteins in the cytosol.

A single colony of *E. coli* strain ER2566 containing pIRAP-CBD or the empty pTYB4 vector coding for only the intein and CDB sequences was inoculated into LB/ampicillin and grown overnight at 37° C. Overnight cultures were used to inoculate (1:5.0) a fresh LB/amp culture which was grown at 37° C. until OD600 was 0.5–0.6. IPTG (1 mM) was added to induce fusion protein expression. Induction of expression was overnight at room temperature. Following induction, cells were collected by centrifugation, resuspended in Buffer 2 [PBS, pH 7.0; 1 mM EDTA; 2 nM AEBSF; 0.1% Triton X-100; 1 M NaCl] and lysed by sonication. Lysates were centrifuged at 4° C. 12,000×g for 30 min. The supernatant was applied to a chitin bead column that was equilibrated in Buffer 2. The pellet was resuspended in Buffer 2 and sonication and centrifugation were repeated. The resulting supernatant was loaded onto the column and the column was washed with >15 column volumes Buffer 2 to reduce nonspecific binding of *E. coli* proteins. Following washing at high salt concentration, the buffer was changed to Buffer 1 [PBS, pH 7.0; 1 mM EDTA; 2 nM AEBSF]. The beads containing IRAP-CBD or CBD alone were removed from the columns and stored at 4° C. as a 25% slurry in PBS/0.02% sodium azide.

For cleavage of the N-terminus of IRAP from the intein-CBD portion of the fusion protein to yield a soluble peptide, the column was quickly flushed with 3 volumes Buffer 1 containing 50 mM DTT, added fresh. The flow was then stopped and the column was incubated for two days at 4° C. to induce cleavage. Three column volumes of Buffer 1 were added to the beads and 1 ml fractions were collected and concentrated using a Microcon-3 device (Amicon). Protein concentration was determined by absorbance at 280 nm.

Cytosol was prepared from fully differentiated 3T3-L1 adipocytes. Cells were placed on ice, washed twice with cold PBS and once with cold HES [250 mM sucrose; 20 mM HEPES, pH 7.4; 5 mM EDTA; 10 µg/ml aprotinin; 1 µg/ml leupeptin, 200 µM AEBSF]. HES (1 ml) was added to each plate and cells were scraped, pooled and lysed by Potter-Elvehjem homogenization. The lysate was centrifuged at 16,000 ×g at 4° C. and the fat cake was removed. The supernatant was centrifugated at 220,000 ×g for 60 min at 4° C. to yield a pellet of internal membranes and the cytosol supernatant. Protein concentration was determined by Bradford assay (BioRad). CBD and IRAP-CBD beads (400 µl each) were added to PolyPrep columns (BioRad) and equilibrated with HES. 3T3-L1 cytosol was precleared by application to the CBD column, the flow-through was applied to the IRAP-CBD column and the column was washed with greater than ten volumes of HES. Proteins were eluted with three column volumes of HES containing 5 µM NT-IRAP peptide. The eluted material was concentrated using a Microcon-3 device (Amicon), solubilized in Laemmli sample buffer, separated by 12% SDS-PAGE and visualized with Bio-Safe Coomassie Blue-G250 (BioRad). Samples of CBD and IRAP-CBD beads and IRAP-NT peptide also were subjected to SDS-PAGE.

The protein gel was washed in HPLC-grade water, stained with Bio-Safe Coomassie Blue-G250 (BioRad) and destained in HPLC-grade water. Protein bands in the 120 kDa region of the gel (and control regions of the gel containing no bands) were excised with a new razor blade and transferred to a 1.5 ml microfuge tube that was rinsed in HPLC-grade water. Gel slices were washed twice with 50% HPLC-grade acetonitrile/HPLC-grade water, the supernatant was removed and the tubes were stored at −80° C. Analysis was performed at the Harvard Microchemistry Facility according to protocols developed there. Tryptic digestion, HPLC and mass spectrometry. Peptide peaks were analyzed by comparison with the database and a protein was identified in the material of approximately 120 kDa that bound to IRAP 1-109 previously identified in the art as (TAP) a 115 kDa protein.

TAP has been described as is a coiled-coil peripheral membrane protein associated with the Golgi and was originally identified as a protein required for vesicle transport within the Golgi (Waters et al., 1992; Yamakawa et al., 1996). Subsequently, TAP has been implicated in the docking of COPI vesicles to the Golgi (Sonnichsen et al., 1998) and of transcytotic vesicles to the plasma membrane (Barroso et al., 1995). It has been proposed that by binding GM103 on Golgi membranes and gigantin on COPI vesicles, p115 TAP functions as a tether protein that bridges transport vesicles to the Golgi (Nakamura et al., 1997; Sonnichsen et al., 1998). In addition, TAP is associated with Golgi membranes in a cell-cycle dependent manner (Levine et al., 1996) and is phosphorylated by casein kinase II (CKII) or a CKII-like kinase (Dirac-Svejstrup et al., 2000).

Example 2

Generation TAP Antibodies and Characterization of TAP Expression and TAP:IRAP Interaction in Adipocytes Peptides were selected and synthesized to generate antibodies to TAP. Selection of candidate peptide sequences based on proposed antigenicity was performed by the outsourcing company BioSource International (formerly QCB). Candidate sequences were analyzed to determine their potential to be in regions of TAP that interact with other proteins, such as gigantin and GM130, two proteins that have been shown to interact with TAP. The following sequences were chosen to generate antibodies that would not interfere with the binding of these proteins: amino acids 40–57 (RNAVRALKSLSKKYRLEV) and 888–905 (LQTEKDKLYLEVTDSKKE). Rabbit polyclonal antibodies were generated and affinity-purified using standard techniques.

By immunoblot using TAP antibodies, p115/TAP was observed in subcellular fractions of rat epididymal adipocytes. p115/TAP was present predominantly in the LDM fraction and did not relocalize to the PM in response to insulin treatment. The LDM is enriched in Golgi and endosomal fractions and is where the insulin-responsive GLUT4/IRAP vesicle population resides. The presence of p115/TAP in the LDM fraction is consistent with results from investigations in other cell systems.

Immunoblots of whole cell lysates of 3T3-L1 cells prepared at two-day intervals during differentiation to adipocytes showed expression of TAP throughout adipogenesis. Furthermore, whole cell lysates of human preadipocytes (day 0) and differentiated preadipocytes (day 21=adipocytes) showed TAP expression.

Co-immunoprecipitations from adipocytes using TAP antiserum followed by immunoblotting for IRAP show the presence of IRAP in these precipitates, indicating that these proteins interact in cells.

Example 3

Characterization of TAP Expression in Adipocytes from Subjects having Diabetes or Insulin Resistance To evaluate the relative expression level of the p115/TAP mRNA among human subjects of different phenotypes, relative quantitative RT-PCR was performed using RNA from human adipocytes and primers specific for the human p115/TAP gene sequence. This system compares the amount of RT-PCR product, which reflects the level of mRNA expression, among individual samples and normalizes the product to the amount of product generated from amplification of the 18S rRNA, which should be constant among samples. Human subjects of different phenotypes where analyzed. Preadipocytes from lean subjects (BMI<25), obese insulin resistant subjects (BMI>30, fasting glucose<110 mg/dL, fasting insulin>30 mU/L), and obese diabetic subjects (BMI>30, diagnosed with type II diabetes) were grown and expanded in culture to the same passage number and then differentiated to adipocytes. Total RNA was then isolated from the adipocytes and used as templates in the relative quantitative RT-PCR using amplification of the 18S rRNA as an internal control. For the reverse transcription reaction random decamers were used, and for the PCR amplification step p115/TAP-specific primers were used. The PCR cycling conditions were optimized for the p115/TAP template.

Figure 3A:
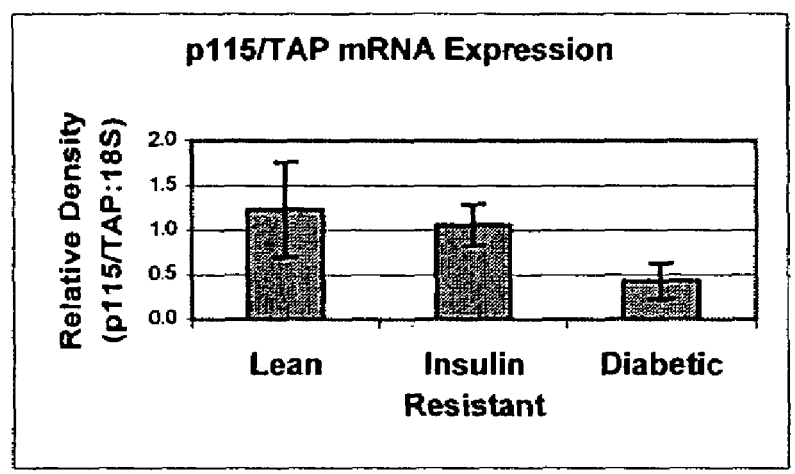
FIG. 3A depicts TAP mRNA expression levels and FIG. 3B depicts TAP protein expression levels.

Using this system, three independent RT-PCRs were performed and reproducible results were obtained. The expression levels of the p115/TAP mRNA in adipocytes from lean and obese insulin resistant subjects were similar. However, the expression of p115/TAP mRNA in cells from obese diabetic subjects was significantly reduced compared to both lean and obese insulin resistant subjects. Data are averaged and presented in FIG. 3A.

Figure 3B:
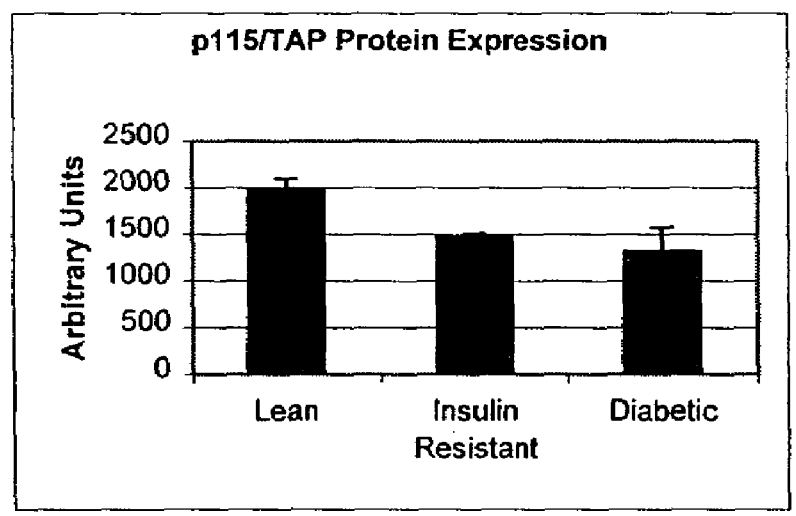

Protein lysates of the differentiated human preadipocytes were also prepared. Equal amounts of protein were subjected to gel electrophoresis and immunoblotting with the p115/TAP antibody described above (i. e., the antibody generated against residues 888–905 of TAP) using standard techniques. Expression of the p115/TAP protein was reduced in insulin resistant and diabetic subjects compared to that in lean control individuals (FIG. 3B).

Example 4

Effect of TAP in Diabetes Disease Models

The foregoing Example demonstrates that TAP expression is decreased or downregulated in subjects having various insulin-related disorders. These data suggest that increasing TAP expression or activity could have important applications for the treatment of, for example, type II diabetes, insulin resistance, obesity and disorders related to obesity. To pursue these potential applications, the following approaches can be taken.

Demonstration of the Efficacy of TAP Activators in Rodent Models of Obesity/Diabetes Rodents, e.g., mice or rats, serving as models for diabetes can be treated with TAP activators to determine whether activation of TAP reduces or ameliorates the symptoms of either diabetes (or insulin resistance) in these animals.

Rodents with diabetes are treated with one or more TAP activators in a therapeutically effective dose. TAP levels in treated and control rodents can be assessed by Western blot analysis using antibodies specific for TAP. Levels of molecules characteristic for diabetes or insulin resistance, such as glucose, insulin, lipids, and creatine kinase can be assessed in serum samples taken from treated and control animals. Functional assays for diabetes including, but not limited to, an insulin sensitivity assay, a glucose tolerance assay and an ex-vivo glucose uptake by isolated muscle cell assay can be performed to monitor the effect of the activator on treated and non-treated animals. Moreover, body weight, and/or fat pad weights can be assayed in these animals. Similarly, muscle and fat cell differentiation can be observed in these animals. Analysis of such studies should enable a determination of the overall effect of the activation of TAP on the progression of diabetes in animal models of the disease.

References cited herein are detailed below:
Barroso M, Nelson D S and Sztul E (1995) Proc. Natl. Acad. Sci. U.S.A. 95:527–531.
Bennett R G, Duckworth W C and Hamel F G (2000) J. Biol. Chem. 275:36621–36625.
Chesneau V, Vekrellis K, Rosner M R and Selkoe D J (2000) Biochem. J. 351:509–516.
Chesneau V, Perlman R G, Keller G A and Rosner M R (1997) Endocrinology 138:3444–3451.
Dirac-Svejstrup A B, Shorter J, Waters M G and Warren G (2000) J. Cell Biol. 150:472–487.
Duckworth W C, Bennet R B and Hamel G H (1998) Endocrine Reviews. 19:608–624.
Fakhrai-Rad H, Nikoshkov A, Kamel A, Fernstrom M, Zierath J, Norgren S, Luthman H and Galli J (2000) Hum. Molec. Genet. 9:2149–2158.
Levine T P, Rabouille C, Kieckbusch R H and Warren G (1996) J. Biol. Chem. 271:17304–17311.
NakamuraN, Lowe M. Levine T R, Rabouille C and Warren G (1997) Cell 89:445–455.
Sonnichsen B, Lowe M. Levine T, Jamsa E, Dirac-Svejstrup B and Warren G (1998) J. Cell Biol. 140:1013–1021.
Waters M G, Clary D O and Rothman J E (1992) J. Cell Biol. 118:1015–1026.
Yamakawa H, Seog D H, Yoda K, Yamasaki M and Wakabayashi T (1996) J. Struct. Biol. 116:356–365.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying an insulin response modulator, comprising contacting a composition comprising insulin-responsive aminopeptidase (IRAP) and human trancytosis-associated protein (TAP) with a test compound and determining the ability of the test compound to modulate binding of IRAP to the human TAP, such that an insulin response modulator is identified.

2. A method for identifying an insulin response modulator, comprising contacting a donor vesicle fraction comprising glucose transporter 4 (GLUT4) vesicles with a test compound and determining the ability of the test compound to modulate GLUT4 vesicle translocation, such that an insulin response modulator is identified, wherein said donor vesicle fraction is associated with human TAP prior to contacting with said test compound.

3. The method of claim 2, wherein determining the ability of the test compound to modulate GLUT4 vesicle translocation comprises detecting translocation of a GLUT4 vesicle component to an acceptor vesicle fraction.

4. The method of claim 3, wherein determining the ability of the test compound to modulate GLUT4 vesicle translocation comprises detecting a change in GLUT4 levels in said acceptor vesicle fraction.

5. The method of claim 4, wherein detecting a change in GLUT4 levels in said acceptor vesicle fraction comprises detecting GLUT4 levels in said acceptor vesicle fraction after contacting said donor vesicle fraction with the test compound as compared to a control acceptor vesicle fraction.

6. The method of claim 3, wherein determining the ability of the test compound to modulate GLUT4 vesicle translocation comprises detecting a change in IRAP levels in said acceptor vesicle fraction.

7. The method of claim 6, wherein detecting a change in IRAP levels in said acceptor vesicle fraction comprises detecting IRAP levels in said acceptor vesicle fraction after contacting said donor vesicle fraction with the test compound as compared to a control acceptor vesicle fraction.

8. The method of any one of claims 2–7, wherein said donor vesicle fraction is a GLUT4 vesicle preparation or a low density microsomal fraction.

9. The method of any one of claims 3–7, wherein said acceptor vesicle fraction is a plasma membrane fraction.

10. The method of any one of claims 3–7, wherein said acceptor vesicle fraction is a plasma membrane fraction and said donor vesicle fraction is a GLUT4 vesicle preparation or a low density microsomal fraction.

11. The method of any one of claims 3–7, wherein determining the ability of the test compound to modulate GLUT4 vesicle translocation comprises detecting fluorescence resonance energy transfer from a component of the donor vesicle fraction to a component of the acceptor vesicle fraction.

12. The method of claim any of claims 1–2, wherein the modulator identified is a positive modulator.

13. A method for identifying an IRAP:human TAP modulator, comprising contacting a composition comprising IRAP and human TAP with a test compound and determining the ability of the test compound to inhibit binding of the IRAP to the human TAP, such that the modulator is identified.

14. A method for identifying an IRAP:human TAP modulator, comprising contacting a composition comprising IRAP and human TAP with a test compound and determining the ability of the test compound to enhance binding of the IRAP to the human TAP, such that the modulator is identified.

* * * * *

SEQUENCE LISTING

```
<160> NUMBER OF SEQ ID NOS: 3

<210> SEQ ID NO 1
<211> LENGTH: 1025
<212> TYPE: PRT
<213> ORGANISM: Homo sapiens

<400> SEQUENCE: 1

Met Glu Pro Phe Thr Asn Asp Arg Leu Gln Leu Pro Arg Asn Met Ile
1               5                   10                  15

Glu Asn Ser Met Phe Glu Glu Glu Pro Asp Val Val Asp Leu Ala Lys
            20                  25                  30

Glu Pro Cys Leu His Pro Leu Glu Pro Asp Glu Val Glu Tyr Glu Pro
        35                  40                  45

Arg Gly Ser Arg Leu Leu Val Arg Gly Leu Gly Glu His Glu Met Glu
    50                  55                  60

Glu Asp Glu Glu Asp Tyr Glu Ser Ser Ala Lys Leu Leu Gly Met Ser
65                  70                  75                  80
```

-continued

```
Phe Met Asn Arg Ser Ser Gly Leu Arg Asn Ser Ala Thr Gly Tyr Arg
                85                  90                  95

Gln Ser Pro Asp Gly Ala Cys Ser Val Pro Ser Ala Arg Thr Met Val
            100                 105                 110

Val Cys Ala Phe Val Ile Val Ala Val Ser Val Ile Met Val Ile
        115                 120                 125

Tyr Leu Leu Pro Arg Cys Thr Phe Thr Lys Glu Gly Cys His Lys Lys
    130                 135                 140

Asn Gln Ser Ile Gly Leu Ile Gln Pro Phe Ala Thr Asn Gly Lys Leu
145                 150                 155                 160

Phe Pro Trp Ala Gln Ile Arg Leu Pro Thr Ala Val Val Pro Leu Arg
                165                 170                 175

Tyr Glu Leu Ser Leu His Pro Asn Leu Thr Ser Met Thr Phe Arg Gly
            180                 185                 190

Ser Val Thr Ile Ser Val Gln Ala Leu Gln Val Thr Trp Asn Ile Ile
        195                 200                 205

Leu His Ser Thr Gly His Asn Ile Ser Arg Val Thr Phe Met Ser Ala
    210                 215                 220

Val Ser Ser Gln Glu Lys Gln Ala Glu Ile Leu Glu Tyr Ala Tyr His
225                 230                 235                 240

Gly Gln Ile Ala Ile Val Ala Pro Glu Ala Leu Leu Ala Gly His Asn
                245                 250                 255

Tyr Thr Leu Lys Ile Glu Tyr Ser Ala Asn Ile Ser Ser Tyr Tyr
            260                 265                 270

Gly Phe Tyr Gly Phe Ser Tyr Thr Asp Glu Ser Asn Glu Lys Lys Tyr
        275                 280                 285

Phe Ala Ala Thr Gln Phe Glu Pro Leu Ala Ala Arg Ser Ala Phe Pro
    290                 295                 300

Cys Phe Asp Glu Pro Ala Phe Lys Ala Thr Phe Ile Ile Lys Ile Ile
305                 310                 315                 320

Arg Asp Glu Gln Tyr Thr Ala Leu Ser Asn Met Pro Lys Lys Ser Ser
                325                 330                 335

Val Val Leu Asp Asp Gly Leu Val Gln Asp Glu Phe Ser Glu Ser Val
            340                 345                 350

Lys Met Ser Thr Tyr Leu Val Ala Phe Ile Val Gly Glu Met Lys Asn
        355                 360                 365

Leu Ser Gln Asp Val Asn Gly Thr Leu Val Ser Ile Tyr Ala Val Pro
    370                 375                 380

Glu Lys Ile Gly Gln Val His Tyr Ala Leu Glu Thr Thr Val Lys Leu
385                 390                 395                 400

Leu Glu Phe Phe Gln Asn Tyr Phe Glu Ile Gln Tyr Pro Leu Lys Lys
                405                 410                 415

Leu Asp Leu Val Ala Ile Pro Asp Phe Glu Ala Gly Ala Met Glu Asn
            420                 425                 430

Trp Gly Leu Leu Thr Phe Arg Glu Glu Thr Leu Leu Tyr Asp Ser Asn
        435                 440                 445

Thr Ser Ser Met Ala Asp Arg Lys Leu Val Thr Lys Ile Ile Ala His
    450                 455                 460

Glu Leu Ala His Gln Trp Phe Gly Asn Leu Val Thr Met Lys Trp Trp
465                 470                 475                 480

Asn Asp Leu Trp Leu Asn Glu Gly Phe Ala Thr Phe Met Glu Tyr Phe
                485                 490                 495

Ser Leu Glu Lys Ile Phe Lys Glu Leu Ser Ser Tyr Glu Asp Phe Leu
```

-continued

```
                500                 505                 510
Asp Ala Arg Phe Lys Thr Met Lys Lys Asp Ser Leu Asn Ser Ser His
            515                 520                 525
Pro Ile Ser Ser Ser Val Gln Ser Ser Glu Ile Glu Glu Met Phe
        530                 535                 540
Asp Ser Leu Ser Tyr Phe Lys Gly Ser Ser Leu Leu Met Leu Lys
545                 550                 555                 560
Thr Tyr Leu Ser Glu Asp Val Phe Gln His Ala Val Leu Tyr Leu
                565                 570                 575
His Asn His Ser Tyr Ala Ser Ile Gln Ser Asp Asp Leu Trp Asp Ser
            580                 585                 590
Phe Asn Glu Val Thr Asn Gln Thr Leu Asp Val Lys Arg Met Met Lys
        595                 600                 605
Thr Trp Thr Leu Gln Lys Gly Phe Pro Leu Val Thr Val Gln Lys Lys
        610                 615                 620
Gly Lys Glu Leu Phe Ile Gln Gln Glu Arg Phe Phe Leu Asn Met Lys
625                 630                 635                 640
Pro Glu Ile Gln Pro Ser Asp Thr Ser Tyr Leu Trp His Ile Pro Leu
                645                 650                 655
Ser Tyr Val Thr Glu Gly Arg Asn Tyr Ser Lys Tyr Gln Ser Val Ser
                660                 665                 670
Leu Leu Asp Lys Lys Ser Gly Val Ile Asn Leu Thr Glu Glu Val Leu
            675                 680                 685
Trp Val Lys Val Asn Ile Asn Met Asn Gly Tyr Tyr Ile Val His Tyr
        690                 695                 700
Ala Asp Asp Asp Trp Glu Ala Leu Ile His Gln Leu Lys Ile Asn Pro
705                 710                 715                 720
Tyr Val Leu Ser Asp Lys Asp Arg Ala Asn Leu Ile Asn Asn Ile Phe
                725                 730                 735
Glu Leu Ala Gly Leu Gly Lys Val Pro Leu Lys Arg Ala Phe Asp Leu
            740                 745                 750
Ile Asn Tyr Leu Gly Asn Glu Asn His Thr Ala Pro Ile Thr Glu Ala
        755                 760                 765
Leu Phe Gln Thr Asp Leu Ile Tyr Asn Leu Leu Glu Lys Leu Gly Tyr
        770                 775                 780
Met Asp Leu Ala Ser Arg Leu Val Thr Arg Val Phe Lys Leu Leu Gln
785                 790                 795                 800
Asn Gln Ile Gln Gln Gln Thr Trp Thr Asp Glu Gly Thr Pro Ser Met
                805                 810                 815
Arg Glu Leu Arg Ser Ala Leu Leu Glu Phe Ala Cys Thr His Asn Leu
            820                 825                 830
Gly Asn Cys Ser Thr Thr Ala Met Lys Leu Phe Asp Asp Trp Met Ala
            835                 840                 845
Ser Asn Gly Thr Gln Ser Leu Pro Thr Asp Val Met Thr Thr Val Phe
        850                 855                 860
Lys Val Gly Ala Lys Thr Asp Lys Gly Trp Ser Phe Leu Leu Gly Lys
865                 870                 875                 880
Tyr Ile Ser Ile Gly Ser Glu Ala Glu Lys Asn Lys Ile Leu Glu Ala
                885                 890                 895
Leu Ala Ser Ser Glu Asp Val Arg Lys Leu Tyr Trp Leu Met Lys Ser
            900                 905                 910
Ser Leu Asn Gly Asp Asn Phe Arg Thr Gln Lys Leu Ser Phe Ile Ile
        915                 920                 925
```

-continued

Arg Thr Val Gly Arg His Phe Pro Gly His Leu Leu Ala Trp Asp Phe
    930                 935                 940

Val Lys Glu Asn Trp Asn Lys Leu Val Gln Lys Phe Pro Leu Gly Ser
945                 950                 955                 960

Tyr Thr Ile Gln Asn Ile Val Ala Gly Ser Thr Tyr Leu Phe Ser Thr
            965                 970                 975

Lys Thr His Leu Ser Glu Val Gln Ala Phe Phe Glu Asn Gln Ser Glu
                980                 985                 990

Ala Thr Phe Arg Leu Arg Cys Val Gln Glu Ala Leu Glu Val Ile Gln
            995                 1000                1005

Leu Asn Ile Gln Trp Met Glu Lys Asn Leu Lys Ser Leu Thr Trp Trp
    1010                1015                1020

Leu
1025

<210> SEQ ID NO 2
<211> LENGTH: 1025
<212> TYPE: PRT
<213> ORGANISM: Rattus norvegicus

<400> SEQUENCE: 2

Met Glu Thr Phe Thr Asn Asp Arg Leu Gln Leu Pro Arg Asn Met Ile
1               5                   10                  15

Glu Asn Ser Met Phe Glu Glu Pro Asp Val Val Asp Leu Ala Lys
            20                  25                  30

Glu Pro Cys Leu His Pro Leu Glu Pro Asp Glu Val Glu Tyr Glu Pro
        35                  40                  45

Arg Gly Ser Arg Leu Leu Val Arg Gly Leu Gly Glu His Glu Met Asp
    50                  55                  60

Glu Asp Glu Glu Asp Tyr Glu Ser Ser Ala Lys Leu Leu Gly Met Ser
65                  70                  75                  80

Phe Met Asn Arg Ser Ser Gly Leu Arg Asn Ser Ala Thr Gly Tyr Arg
                85                  90                  95

Gln Ser Pro Asp Gly Thr Cys Ser Val Pro Ser Ala Arg Thr Leu Val
            100                 105                 110

Ile Cys Val Phe Val Ile Val Val Ala Val Ser Val Ile Met Val Ile
        115                 120                 125

Tyr Leu Leu Pro Arg Cys Thr Phe Thr Lys Glu Gly Cys His Lys Thr
    130                 135                 140

Asn Gln Ser Ala Glu Leu Ile Gln Pro Ile Ala Thr Asn Gly Lys Val
145                 150                 155                 160

Phe Pro Trp Ala Gln Ile Arg Leu Pro Thr Ala Ile Ile Pro Gln Arg
                165                 170                 175

Tyr Glu Leu Ser Leu His Pro Asn Leu Thr Ser Met Thr Phe Arg Gly
            180                 185                 190

Ser Val Thr Ile Ser Leu Gln Ala Leu Gln Asp Thr Arg Asp Ile Ile
        195                 200                 205

Leu His Ser Thr Gly His Asn Ile Ser Ser Val Thr Phe Met Ser Ala
    210                 215                 220

Val Ser Ser Gln Glu Lys Gln Val Glu Ile Leu Glu Tyr Pro Tyr His
225                 230                 235                 240

Glu Gln Ile Ala Val Val Ala Pro Glu Ser Leu Leu Thr Gly His Asn
                245                 250                 255

Tyr Thr Leu Lys Ile Glu Tyr Ser Ala Asn Ile Ser Asn Ser Tyr Tyr

-continued

```
                 260                 265                 270
Gly Phe Tyr Gly Ile Thr Tyr Thr Asp Lys Ser Asn Glu Lys Lys Asn
            275                 280                 285

Phe Ala Ala Thr Gln Phe Glu Pro Leu Ala Ala Arg Ser Ala Phe Pro
        290                 295                 300

Cys Phe Asp Glu Pro Ala Phe Lys Ala Thr Phe Ile Lys Ile Thr
305                 310                 315                 320

Arg Asp Glu His His Thr Ala Leu Ser Asn Met Pro Lys Lys Ser Ser
                325                 330                 335

Val Pro Thr Glu Glu Gly Leu Ile Gln Asp Glu Phe Ser Glu Ser Val
            340                 345                 350

Lys Met Ser Thr Tyr Leu Val Ala Phe Ile Val Gly Glu Met Arg Asn
            355                 360                 365

Leu Ser Gln Asp Val Asn Gly Thr Leu Val Ser Val Tyr Ala Val Pro
        370                 375                 380

Glu Lys Ile Asp Gln Val Tyr His Ala Leu Asp Thr Thr Val Lys Leu
385                 390                 395                 400

Leu Glu Phe Tyr Gln Asn Tyr Phe Glu Ile Gln Tyr Pro Leu Lys Lys
                405                 410                 415

Leu Asp Leu Val Ala Ile Pro Asp Phe Glu Ala Gly Ala Met Glu Asn
            420                 425                 430

Trp Gly Leu Leu Thr Phe Arg Glu Glu Thr Leu Leu Tyr Asp Asn Ala
        435                 440                 445

Thr Ser Ser Val Ala Asp Arg Lys Leu Val Thr Lys Ile Ile Ala His
        450                 455                 460

Glu Leu Ala His Gln Trp Phe Gly Asn Leu Val Thr Met Gln Trp Trp
465                 470                 475                 480

Asn Asp Leu Trp Leu Asn Glu Gly Phe Ala Thr Phe Met Glu Tyr Phe
                485                 490                 495

Ser Val Glu Lys Ile Phe Lys Glu Leu Asn Ser Tyr Glu Asp Phe Leu
            500                 505                 510

Asp Ala Arg Phe Lys Thr Met Arg Lys Asp Ser Leu Asn Ser Ser His
        515                 520                 525

Pro Ile Ser Ser Val Gln Ser Ser Glu Gln Ile Glu Glu Met Phe
        530                 535                 540

Asp Ser Leu Ser Tyr Phe Lys Gly Ala Ser Leu Leu Met Leu Lys
545                 550                 555                 560

Ser Tyr Leu Ser Glu Asp Val Phe Gln His Ala Ile Ile Leu Tyr Leu
            565                 570                 575

His Asn His Ser Tyr Ala Ala Ile Gln Ser Asp Asp Leu Trp Asp Ser
                580                 585                 590

Phe Asn Glu Val Thr Gly Lys Thr Leu Asp Val Lys Lys Met Met Lys
        595                 600                 605

Thr Trp Thr Leu Gln Lys Gly Phe Pro Leu Val Thr Val Gln Arg Lys
        610                 615                 620

Gly Thr Glu Leu Leu Leu Gln Glu Arg Phe Phe Pro Ser Met Gln
625                 630                 635                 640

Pro Glu Ile Gln Asp Ser Asp Thr Ser His Leu Trp His Ile Pro Ile
                645                 650                 655

Ser Tyr Val Thr Asp Gly Arg Asn Tyr Ser Glu Tyr Arg Ser Val Ser
            660                 665                 670

Leu Leu Asp Lys Lys Ser Asp Val Ile Asn Leu Thr Glu Gln Val Gln
        675                 680                 685
```

```
Trp Val Lys Val Asn Thr Asn Met Thr Gly Tyr Tyr Ile Val His Tyr
    690                 695                 700
Ala His Asp Gly Trp Ala Ala Leu Ile Asn Gln Leu Lys Arg Asn Pro
705                 710                 715                 720
Tyr Val Leu Ser Asp Lys Asp Arg Ala Asn Leu Ile Asn Asn Ile Phe
                725                 730                 735
Glu Leu Ala Gly Leu Gly Lys Val Pro Leu Gln Met Ala Phe Asp Leu
            740                 745                 750
Ile Asp Tyr Leu Arg Asn Glu Thr His Thr Ala Pro Ile Thr Glu Ala
        755                 760                 765
Leu Phe Gln Thr Asp Leu Ile Tyr Asn Leu Leu Glu Lys Leu Gly His
    770                 775                 780
Met Asp Leu Ser Ser Arg Leu Val Thr Arg Val His Lys Leu Leu Gln
785                 790                 795                 800
Asn Gln Ile Gln Gln Gln Thr Trp Thr Asp Glu Gly Thr Pro Ser Met
                805                 810                 815
Arg Glu Leu Arg Ser Ala Leu Leu Glu Phe Ala Cys Ala His Ser Leu
            820                 825                 830
Glu Asn Cys Thr Thr Met Ala Thr Lys Leu Phe Asp Gly Trp Met Ala
        835                 840                 845
Ser Asn Gly Thr Gln Ser Leu Pro Thr Asp Val Met Thr Thr Val Phe
    850                 855                 860
Lys Val Gly Ala Arg Thr Glu Lys Gly Trp Leu Phe Leu Phe Ser Met
865                 870                 875                 880
Tyr Ser Ser Met Gly Ser Glu Ala Glu Lys Asp Lys Ile Leu Glu Ala
                885                 890                 895
Leu Ala Ser Ser Ala Asp Ala His Lys Leu Tyr Trp Leu Met Lys Ser
            900                 905                 910
Ser Leu Asp Gly Asp Ile Ile Arg Thr Gln Lys Leu Ser Leu Ile Ile
        915                 920                 925
Arg Thr Val Gly Arg Gln Phe Pro Gly His Leu Leu Ala Trp Asp Phe
    930                 935                 940
Val Lys Glu Asn Trp Asn Lys Leu Val His Lys Phe His Leu Gly Ser
945                 950                 955                 960
Tyr Thr Ile Gln Ser Ile Val Ala Gly Ser Thr His Leu Phe Ser Thr
                965                 970                 975
Lys Thr His Leu Ser Glu Val Gln Glu Phe Phe Glu Asn Gln Ser Glu
            980                 985                 990
Ala Thr Leu Gln Leu Arg Cys Val Gln Glu Ala Phe Glu Val Ile Glu
        995                 1000                1005
Leu Asn Ile Gln Trp Met Ala Arg Asn Leu Lys Thr Leu Thr Leu Trp
    1010                1015                1020
Leu
1025

<210> SEQ ID NO 3
<211> LENGTH: 962
<212> TYPE: PRT
<213> ORGANISM: Homo sapiens

<400> SEQUENCE: 3

Met Asn Phe Leu Arg Gly Val Met Gly Gly Gln Ser Ala Gly Pro Gln
1               5                   10                  15

His Thr Glu Ala Glu Thr Ile Gln Lys Leu Cys Asp Arg Val Ala Ser
```

-continued

```
                    20                  25                  30
Ser Thr Leu Leu Asp Asp Arg Arg Asn Ala Val Arg Ala Leu Lys Ser
                35                  40                  45
Leu Ser Lys Lys Tyr Arg Leu Glu Val Gly Ile Gln Ala Met Glu His
            50                  55                  60
Leu Ile His Val Leu Gln Thr Asp Arg Ser Asp Ser Glu Ile Ile Gly
 65                  70                  75                  80
Tyr Ala Leu Asp Ile Leu Tyr Asn Ile Ile Ser Asn Glu Glu Glu Glu
                85                  90                  95
Glu Val Glu Glu Asn Ser Thr Arg Gln Ser Glu Asp Leu Gly Ser Gln
            100                 105                 110
Phe Thr Glu Ile Phe Ile Lys Gln Gln Glu Asn Val Thr Leu Leu Leu
            115                 120                 125
Ser Leu Leu Glu Glu Phe Asp Phe His Val Arg Trp Pro Gly Val Lys
            130                 135                 140
Leu Leu Thr Ser Leu Leu Lys Gln Leu Gly Pro Gln Val Gln Gln Ile
145                 150                 155                 160
Ile Leu Val Ser Pro Met Gly Val Ser Arg Leu Met Asp Leu Leu Ala
                165                 170                 175
Asp Ser Arg Glu Val Ile Arg Asn Asp Gly Val Leu Leu Leu Gln Ala
            180                 185                 190
Leu Thr Arg Ser Asn Gly Ala Ile Gln Lys Ile Val Ala Phe Glu Asn
        195                 200                 205
Ala Phe Glu Arg Leu Leu Asp Ile Ile Ser Glu Gly Asn Ser Asp
    210                 215                 220
Gly Gly Ile Val Val Glu Asp Cys Leu Ile Leu Leu Gln Asn Leu Leu
225                 230                 235                 240
Lys Asn Asn Ser Asn Gln Asn Phe Phe Lys Glu Gly Ser Tyr Ile
                245                 250                 255
Gln Arg Met Lys Pro Trp Phe Glu Val Gly Asp Glu Asn Ser Gly Trp
            260                 265                 270
Ser Ala Gln Lys Val Thr Asn Leu His Leu Met Leu Gln Leu Val Arg
        275                 280                 285
Val Leu Val Ser Pro Thr Asn Pro Pro Gly Ala Thr Ser Ser Cys Gln
    290                 295                 300
Lys Ala Met Phe Gln Cys Gly Leu Leu Gln Gln Leu Cys Thr Ile Leu
305                 310                 315                 320
Met Ala Thr Gly Val Pro Ala Asp Ile Leu Thr Glu Thr Ile Asn Thr
                325                 330                 335
Val Ser Glu Val Ile Arg Gly Cys Gln Val Asn Gln Asp Tyr Phe Ala
            340                 345                 350
Ser Val Asn Ala Pro Ser Asn Pro Pro Arg Pro Ala Ile Val Val Leu
        355                 360                 365
Leu Met Ser Met Val Asn Glu Arg Gln Pro Phe Val Leu Arg Cys Ala
    370                 375                 380
Val Leu Tyr Cys Phe Gln Cys Phe Leu Tyr Lys Asn Gln Lys Gly Gln
385                 390                 395                 400
Gly Glu Ile Val Ser Thr Leu Leu Pro Ser Thr Ile Asp Ala Thr Gly
                405                 410                 415
Asn Ser Val Ser Ala Gly Gln Leu Leu Cys Gly Gly Leu Phe Ser Thr
            420                 425                 430
Asp Ser Leu Ser Asn Trp Cys Ala Ala Val Ala Leu Ala His Ala Leu
        435                 440                 445
```

```
Gln Glu Asn Ala Thr Gln Lys Glu Gln Leu Leu Arg Val Gln Leu Ala
    450                 455                 460
Thr Ser Ile Gly Asn Pro Val Ser Leu Leu Gln Gln Cys Thr Asn
465                 470                 475                 480
Ile Leu Ser Gln Gly Ser Lys Ile Gln Thr Arg Val Gly Leu Leu Met
                485                 490                 495
Leu Leu Cys Thr Trp Leu Ser Asn Cys Pro Ile Ala Val Thr His Phe
            500                 505                 510
Leu His Asn Ser Ala Asn Val Pro Phe Leu Thr Gly Gln Ile Ala Glu
        515                 520                 525
Asn Leu Gly Glu Glu Gln Leu Val Gln Gly Leu Cys Ala Leu Leu
    530                 535                 540
Leu Gly Ile Ser Ile Tyr Phe Asn Asp Asn Ser Leu Glu Ser Tyr Met
545                 550                 555                 560
Lys Glu Lys Leu Lys Gln Leu Ile Glu Lys Arg Ile Gly Lys Glu Asn
                565                 570                 575
Phe Ile Glu Lys Leu Gly Phe Ile Ser Lys His Glu Leu Tyr Ser Arg
            580                 585                 590
Ala Ser Gln Lys Pro Gln Pro Asn Phe Pro Ser Pro Glu Tyr Met Ile
        595                 600                 605
Phe Asp His Glu Phe Thr Lys Leu Val Lys Glu Leu Glu Gly Val Ile
    610                 615                 620
Thr Lys Ala Ile Tyr Lys Ser Glu Glu Asp Lys Lys Glu Glu Glu
625                 630                 635                 640
Val Lys Lys Thr Leu Glu Gln His Asp Asn Ile Val Thr His Tyr Lys
                645                 650                 655
Asn Met Ile Arg Glu Gln Asp Leu Gln Leu Glu Glu Leu Arg Gln Gln
            660                 665                 670
Val Ser Thr Leu Lys Cys Gln Asn Glu Gln Leu Gln Thr Ala Val Thr
        675                 680                 685
Gln Gln Val Ser Gln Ile Gln Gln His Lys Asp Gln Tyr Asn Leu Leu
    690                 695                 700
Lys Ile Gln Leu Gly Lys Asp Asn His Gln Gly Ser Tyr Ser Glu
705                 710                 715                 720
Gly Ala Gln Met Asn Gly Ile Gln Pro Glu Glu Ile Gly Arg Leu Arg
                725                 730                 735
Glu Glu Ile Glu Glu Leu Lys Arg Asn Gln Glu Leu Leu Gln Ser Gln
            740                 745                 750
Leu Thr Glu Lys Asp Ser Met Ile Glu Asn Met Lys Ser Ser Gln Thr
        755                 760                 765
Ser Gly Thr Asn Glu Gln Ser Ser Ala Ile Val Ser Ala Arg Asp Ser
    770                 775                 780
Glu Gln Val Ala Glu Leu Lys Gln Glu Leu Ala Thr Leu Lys Ser Gln
785                 790                 795                 800
Leu Asn Ser Gln Ser Val Glu Ile Thr Lys Leu Gln Thr Glu Lys Gln
                805                 810                 815
Glu Leu Leu Gln Lys Thr Glu Ala Phe Ala Lys Ser Val Glu Val Gln
            820                 825                 830
Gly Glu Thr Glu Thr Ile Ile Ala Thr Lys Thr Asp Val Glu Gly
        835                 840                 845
Arg Leu Ser Ala Leu Leu Gln Glu Thr Lys Glu Leu Lys Asn Glu Ile
    850                 855                 860
```

-continued

```
Lys Ala Leu Ser Glu Glu Arg Thr Ala Ile Lys Glu Gln Leu Asp Ser
865                 870                 875                 880

Ser Asn Ser Thr Ile Ala Ile Leu Gln Thr Glu Lys Asp Lys Leu Glu
                885                 890                 895

Leu Glu Ile Thr Asp Ser Lys Lys Glu Gln Asp Asp Leu Leu Val Leu
                900                 905                 910

Leu Ala Asp Gln Asp Gln Lys Ile Leu Ser Leu Lys Asn Lys Leu Lys
                915                 920                 925

Asp Leu Gly His Pro Val Glu Glu Glu Asp Glu Leu Glu Ser Gly Asp
        930                 935                 940

Gln Glu Asp Glu Asp Asp Glu Ser Glu Asp Pro Gly Lys Asp Leu Asp
945                 950                 955                 960

His Ile
```